(12) United States Patent
Vainio et al.

(10) Patent No.: US 9,890,403 B2
(45) Date of Patent: Feb. 13, 2018

(54) METHOD FOR PRODUCING SINGLE CELL OIL FROM LIGNOCELLULOSIC MATERIALS

(71) Applicant: NESTE OYJ, Espoo (FI)

(72) Inventors: Heidi Vainio, Espoo (FI); Mika Sipponen, Espoo (FI); Simo Laakso, Turku (FI); Ossi Pastinen, Kantvik (FI); Ilkka Lehtomäki, Helsinki (FI); Perttu Koskinen, Helsinki (FI); Miia Laamanen, Helsinki (FI)

(73) Assignee: NESTE OYJ, Espoo (FI)

( * ) Notice: Subject to any disclaimer, the term of this patent is extended or adjusted under 35 U.S.C. 154(b) by 0 days.

(21) Appl. No.: 15/103,675

(22) PCT Filed: Dec. 11, 2014

(86) PCT No.: PCT/EP2014/077462
§ 371 (c)(1),
(2) Date: Jun. 10, 2016

(87) PCT Pub. No.: WO2015/086780
PCT Pub. Date: Jun. 18, 2015

(65) Prior Publication Data
US 2016/0304914 A1    Oct. 20, 2016

(30) Foreign Application Priority Data

Dec. 11, 2013  (EP) .................... 13196743

(51) Int. Cl.
| C12N 1/38 | (2006.01) |
| C12P 7/64 | (2006.01) |
| C12N 1/14 | (2006.01) |
| C12N 1/22 | (2006.01) |
| C12N 1/16 | (2006.01) |
| C12N 1/20 | (2006.01) |

(52) U.S. Cl.
CPC .............. *C12P 7/6463* (2013.01); *C12N 1/14* (2013.01); *C12N 1/16* (2013.01); *C12N 1/20* (2013.01); *C12N 1/22* (2013.01); *C12P 2203/00* (2013.01); *Y02E 50/13* (2013.01)

(58) Field of Classification Search
None
See application file for complete search history.

(56) References Cited

U.S. PATENT DOCUMENTS

| 7,691,792 B1 | 4/2010 | Fisher et al. | |
| 8,697,403 B2 * | 4/2014 | Holmback | C12N 1/38 435/134 |
| 8,900,832 B2 * | 12/2014 | Kahelin | C11B 1/025 435/134 |
| 9,441,252 B2 * | 9/2016 | Singh | C11L 31/04 |
| 2008/0032344 A1 | 2/2008 | Fallavollita | |
| 2009/0004715 A1 | 1/2009 | Trimbur et al. | |
| 2009/0011480 A1 | 1/2009 | Trimbur et al. | |
| 2009/0035842 A1 | 2/2009 | Trimbur et al. | |
| 2009/0047721 A1 | 2/2009 | Trimbur et al. | |
| 2009/0061493 A1 | 3/2009 | Trimbur et al. | |
| 2009/0148918 A1 | 6/2009 | Trimbur et al. | |
| 2010/0323413 A1 | 12/2010 | Trimbur et al. | |
| 2010/0323414 A1 | 12/2010 | Trimbur et al. | |
| 2011/0014665 A1 | 1/2011 | Trimbur et al. | |
| 2011/0015417 A1 | 1/2011 | Trimbur et al. | |
| 2011/0047863 A1 | 3/2011 | Trimbur et al. | |
| 2011/0190522 A1 | 8/2011 | Trimbur et al. | |
| 2011/0217745 A1 | 9/2011 | Li et al. | |
| 2011/0252696 A1 | 10/2011 | Franklin et al. | |
| 2011/0262970 A1 | 10/2011 | Li et al. | |
| 2011/0314726 A1 | 12/2011 | Jameel et al. | |
| 2012/0028319 A1 | 2/2012 | Trimbur et al. | |
| 2012/0036768 A1 | 2/2012 | Phillips et al. | |
| 2012/0122192 A1 | 5/2012 | Trimbur et al. | |
| 2012/0159838 A1 | 6/2012 | Malm et al. | |
| 2012/0159839 A1 | 6/2012 | Koskinen et al. | |
| 2012/0159840 A1 | 6/2012 | Koskinen et al. | |
| 2012/0164701 A1 | 6/2012 | Trimbur et al. | |
| 2012/0288930 A1 | 11/2012 | Trimbur et al. | |
| 2013/0143285 A1 | 6/2013 | Tolan et al. | |
| 2013/0330790 A1 | 12/2013 | Trimbur et al. | |

(Continued)

FOREIGN PATENT DOCUMENTS

| EP | 1 396 531 A2 | 3/2004 |
| EP | 1 398 364 A1 | 3/2004 |

(Continued)

OTHER PUBLICATIONS

Ruan Z. et al. Evaluation of Lipid Accumulation from Lignocellulosic Sugars by Mortierella isabellina for Biodiesel Production. Bioresource Tech 110:198-205, 2012.*
Hu, C. et al. Effects of Biomass Hydrolysis By-Products on Oleaginous Yeast Rhodosporidium toruloides. Bioresource Tech 100(20)4843-4847, Oct. 2009.*
Huang, X. et al. Biological Removal of Inhibitors Leads to the Improved Lipid Production in the Lipid Fermentation of Corn Stover Hydrolysate by Trichosporon cutaneum. Bioresource Tech 102(20)9705-9709, 2011.*
Zhao, X. et al. Effects of Some Inhibitors on the Growth and Lipid Accumulation of Oleaginous Yeast Rhodosporidium toruloids and Preparation of Biodiesel by Enzymatic Transesterification of the Lipid. Bioprocess and Biosystems Engineering 35(6)993-1004, Aug. 2012.*

(Continued)

*Primary Examiner* — Ralph J Gitomer
(74) *Attorney, Agent, or Firm* — Buchanan Ingersoll & Rooney PC

(57) ABSTRACT

The present disclosure relates to methods for producing microbial lipids. The present disclosure also relates to methods for producing microbial lipids using inhibitors obtainable from lignocellulosic materials to suppress the proliferation of unwanted microorganisms in the fermentation broth. The method can therefore reduce the risk of having contaminating microbes establish in the system and the cultivation and thus higher yields of microbial lipids may be obtained.

12 Claims, 3 Drawing Sheets

(56) References Cited

U.S. PATENT DOCUMENTS

2014/0170716 A1  6/2014  Trimbur et al.
2014/0234919 A1  8/2014  Yu et al.

FOREIGN PATENT DOCUMENTS

| EP | 1 741 767 A1 | 1/2007 |
| EP | 1 741 768 A1 | 1/2007 |
| EP | 2 468 857 A1 | 6/2012 |
| EP | 2 468 875 A1 | 6/2012 |
| EP | 2 468 877 A1 | 6/2012 |
| WO | WO 01/32715 A1 | 5/2001 |
| WO | WO 2008/151149 A2 | 12/2008 |
| WO | WO2010/025455 A2 | 3/2010 |
| WO | WO 2010/039783 A2 | 4/2010 |
| WO | WO 2010/060052 A2 | 5/2010 |
| WO | WO 2012/085340 A1 | 6/2012 |
| WO | WO 2013/006755 A2 | 1/2013 |

OTHER PUBLICATIONS

Huang C. et al. Effects of Alcohol Compounds on the Growth and Lipid Accumulation of Oleaginous Yeast Trichosporon fermentans. PLoS One 7(10)1-12, Oct. 5, 2012.*

International Search Report (PCT/ISA/210) dated Feb. 16, 2015, by the Japanese Patent Office as the International Searching Authority for International Application No. PCT/EP2014/077462.

Written Opinion (PCT/ISA/237) dated Feb. 16, 2015, by the Japanese Patent Office as the International Searching Authority for International Application No. PCT/EP2014/077462.

International Search Report (PCT/ISA/210) dated Jan. 28, 2015, by the Japanese Patent Office as the International Searching Authority for International Application No. PCT/EP2014/077464.

Written Opinion (PCT/ISA/237) dated Jan. 28, 2015, by the Japanese Patent Office as the International Searching Authority for International Application No. PCT/EP2014/077464.

International Search Report (PCT/ISA/210) dated Feb. 12, 2015, by the Japanese Patent Office as the International Searching Authority for International Application No. PCT/EP2014/077465.

Written Opinion (PCT/ISA/237) dated Feb. 12, 2015, by the Japanese Patent Office as the International Searching Authority for International Application No. PCT/EP2014/077465.

Barcelos, C.A. et. al., "The Essentialness of Delignification on Enzymatic Hydrolysis of Sugar Cane Bagasse Cellulignin for Second Generation Ethanol Production", Waste and Biomass Valorization, Jun. 21, 2012, pp. 341-346, vol. 4, No. 2. XP055117486.

Muhammad, I. et al., "Effect of Various Pretreatment Conditions on Enzymatic Saccharification", Songklanakarin Journal of Science and Technology, Jul.-Aug. 2011, pp. 397-404, vol. 33, No. 4. XP055117426.

Huang, C. et al., "Microbial Oil Production From Rice Straw Hydrolysate by *Trichosporon fermentans*", Bioresource Technology, Oct. 1, 2009, pp. 4535-4538, vol. 100, No. 19. XP026148880.

Xue- Fang, C. et al., "Microbial Oil Production From Corncob Acid Hydrolysate", Biotechnology Letters, Feb. 16, 2012, pp. 1025-1028, vol. 34, No. 6. XP035047251.

Yu, X. et al., "Oil Production by Oleaginous Yeasts Using The Hydrolysate From Pretreatment of Wheat Straw With Dilute Sulfuric Acid", Bioresource Technology, Feb. 18, 2011, No. 10, pp. 6134-6140, vol. 102. XP028407881.

Ruan, Z. et al., "Evaluation of lipid accumulation from lignocellulosic sugars by *Mortierella isabellina* for biodiesel production", Bioresource Technology, Jan. 28, 2012, pp. 198-205, vol. 110.

Yousuf, A., "Biodiesel from lignocellulosic biomass—Prospects and challenges", Waste Management, Apr. 3, 2012, pp. 2061-2067, vol. 32, No. 11.

Tanaka, M. et al., "Removal of Lignin and Reuse of Cellulases for Continuous Saccharification of Lignocellulos", Biotechnology and Bioengineering, 1988, pp. 897-902, vol. 32.

Harmsen, P. et al., "Literature review of physical and chemical pretreatment processes for lignocellulosic biomass", Wageningen UR Food and Biobased Research, Sep. 2010, pp. 1-48, retrieved from the Internet: http://www.biomassandbioenergy.nl/filesdwnld/Literature%20review_FBR.pdf.

Alvira, P. et al., "Pretreatment technologies for an efficient bioethanol production process based on enzymatic hydrolysis: A review", Bioresource Technology, Dec. 29, 2009, pp. 4851-4861, vol. 101, No. 13.

Huang, HJ et al., "A review of separation technologies in current and future biorefineries", Separation and Purification Technology, Aug. 2008, pp. 1-21, vol. 62, No. 1.

* cited by examiner

METHOD FOR PRODUCING SINGLE CELL OIL FROM LIGNOCELLULOSIC MATERIALS

FIELD OF THE INVENTION

The present invention relates to methods for producing microbial lipids. In particular the present invention relates to methods for producing microbial lipids using inhibitors obtainable from lignocellulosic materials to suppress the proliferation of unwanted microorganisms in the fermentation broth.

BACKGROUND OF THE INVENTION

Lignocellulose is the most abundant biopolymer on earth. Lignocellulose is the major structural component of woody plants and non-woody plants such as grass. Lignocellulosic biomass refers to plant biomass that is composed of cellulose, hemicellulose, and lignin. Large amounts of lignocellulosic residues are produced through forestry, timber and pulp and paper industries and agricultural practices (straw, stover, bagasse, chaff) and many agroindustries. Also municipal waste contains fractions that can be considered as lignocellulose residues, such as paper or cardboard waste, garden waste or waste wood from construction. Due to high abundance and low price lignocellulosic residues are preferred materials for production of biofuels. In addition, dedicated woody or herbaceous energy crops with biomass productivity have gained interest as biofuel use.

The production of biofuels, especially ethanol, from lignocellulosic materials by microbial fermentations has been studied extensively. The greatest challenge for utilization of lignocellulosics for microbiological production of biofuels or biofuel feedstocks lays in the complexity of the lignocellulose material and in its resistance to biodegradation. In lignocellulose, cellulose (20-50% of plant dry weight) fibers are embedded in covalently found matrix of hemicellulose (20-40%), pectin (2-20%) and lignin (10-20%) forming very resistant structure for biodegradation. Further, the sugar residues of hemicellulose contain a varying mixture of hexoses (e.g., glucose, mannose and galactose), and pentoses (e.g., arabinose and xylose) depending on the biomass.

The pre-treatment of lignocellulosic material with high yield to sugars that are utilizable by micro-organisms represents one of the highest challenges. Significant cost reductions are needed in the costs of enzymes needed in hydrolysis of sugar polymers to sugar monomers that are utilizable by desired microorganisms. Further, the economically feasible production of biofuels from lignocellulosic materials requires efficient conversion of all the main carbohydrate constituents of this complex material to biofuels.

Enzymatic hydrolysis of the lignocellulosic material is typically performed in a separate step from biofuel production process by commercial enzymes bought and produced outside the actual biofuel production process.

Certain microorganisms can produce lipids from organic molecules, such as sugars derived from lignocellulose. Certain microorganisms, typically yeast, fungi or bacteria, can efficiently convert both C6 and C5 sugars in lignocellulosic materials to oil. Oil produced by heterotrophic microorganisms is often called as single cell oil or microbial oil. Single cell oil production process using heterotrophic microorganisms comprises cultivating microorganisms in aerated bioreactors, allowing cells to accumulate lipids, harvesting lipid-rich cells and recovering oil from cells. Microorganism-based lipids (i.e. single cell oils) can be used as raw materials for production of biofuels such as biodiesel, renewable diesel or bio jet fuel.

Lignocellulose hydrolysates have been utilized also in the production of single cell oils. Lignocellulose hydrolysis has been typically carried out by pre-treating the lignocellulosic material to monomeric sugars prior feeding to bioprocess.

Patent publication US2009217569 describes single cell oil production from various lignocellulosic and other material hydrolysates, such as straw, wood, pulp and paper industry residues, recycled fibres, municipal waste, algae biomass. Manufacturing biofuel comprises treating source material with water, acid or alkali and contacting filtrate or precipitate with lipid-producing microorganism. Patent publication US2009064567 describes single cell oil production from cellulose material hydrolysates for biodiesel and jet biofuel production by Stramenopiles. US20090011480 describes single cell oil production by heterotrophically grown algae and fungi from depolymerised lignocellulosic materials, such as straw, wood, pulp mill waste, switchgrass. CN101148630 describes single cell oil production from wheat, corn or rice straw hemicellulose hydrolysates, obtained by steam explosion, by bacteria or fungi.

Further, in the prior art has been described lipid production directly from polymeric sugars in lignocellulose, such as xylan by Fall et al. (1984), or cellulose by Lin et al. (2010).

WO2010042842 describes production of single cell oil from lignocellulose hydrolysates by mixed culture of microorganism(s) capable of degrading polymeric sugars in lignocellulose and at least one algae species. The culture is grown in successive aerobic and anaerobic cultivations, where fatty acids are produced from sugars and from anaerobic fermentation products.

WO2010006228 describes sequential production of biofuels from lignocelluloses. In first stage, anaerobic fermentation with organisms capable of producing alcohols from polymeric sugars in lignocellulose hydrolysates, in second stage, the spent culture medium, possibly containing at least one fermentation product, is treated with algae in order to accumulate single-cell oils.

The presence of contaminating non-lipid producing microbes in fermentation broth may influence the oil productivity and yield since the non-lipid producing microbe compete with oil producing microorganisms (oleaginous microbes) on sugars in the lignocellulose hydrolysates and thus making the process less feasible.

There is therefore a need for method of controlling the culture of micro-organisms in the single cell oil production process in such a way that the proliferation of the oleaginous microbes is favoured over the proliferation of non-oleaginous microbes

SUMMARY OF THE INVENTION

The single cell oil production is typically performed by cultivating lipid producing microbes (oleaginous microbes) under aerobic conditions in the presence of a suitable substrate such as lignocellulosic sugars, such as hemicellulosic sugars, obtained by lignocellulose fractionation. The average aerobic fermenter typically has a much lower volume and capacity than the anaerobic fermenters and is more expensive to run. It follows that the demands for efficient cultivation is higher for single cell oil production that rely on cultivation under aerobic conditions. Contamination of the cultivation with microbes that does not produce lipids or only lipids in low amounts may significantly lower the yield and productivity of single cell oil. The presence of contaminating microbes during cultivation should therefore be avoided.

One object of the present invention is therefore to provide a method for single cell oil production that depletes or reduces the amount of contaminating non-lipid producing microbes in the cultivation and thus favours the proliferations of oleaginous microbes.

Lignocellulose fractionation typically produces hemicellulose fraction that contains high concentrations of inhibitor compounds, typically phenolic compounds. In production of single-cell-oil highly concentrated sugar solutions (syrups) are typically required. Thus, the hemicellulose hydrolysates need to be concentrated. Non-volatile inhibitors are concentrated in hydrolysate when the liquid is concentrated by evaporation.

Degradation products are generated in the process of lignocellulose fractionation. Some of these degradations products act as of microbial inhibitors (such as phenolic compounds, organic acids, furfural and hydroxymethylfurfural). The inventors has discovered that by adjustment of the concentration of these microbial inhibitors in accordance to the tolerance of the oleaginious microbes to said inhibitor, the proliferation of the contaminating non-lipid producing microbes may be suppressed.

Accordingly, a first aspect of the present invention relates to a method for producing lipids, comprising the following steps
  (i) providing a cultivation medium comprising a lignocellulosic hydrolysate,
  (ii) providing a fermentation broth by inoculating the cultivation medium of (i) with a first microbe, where said first microbe is an oleaginous microbe,
  (iii) incubating said medium inoculated with said first microbe allowing lipids to accumulate,
wherein said fermentation broth comprises at least one microbial growth inhibitor, and wherein said first microbe is tolerant to said microbial growth inhibitor(s), wherein said incubation is conducted under aerobic conditions.

A second aspect of the present invention relates to a fermentation broth comprising a lignocellulosic hydrolysate, at least one microbial growth inhibitor and an oleaginous microbe, wherein said oleaginous microbe is tolerant to said microbial growth inhibitor(s).

A third aspect relates to the use of the fermentation broth of the present invention in a method for producing a lipid.

A fourth aspect relates to the use of a composition comprising at least one microbial growth inhibitor in a method for producing a lipid, wherein the lipid is produced and accumulates in an oleaginous microbe and wherein said oleaginous microbe is tolerant to said at least one microbial growth inhibitor.

DETAILED DESCRIPTION OF THE INVENTION

Figure 1:
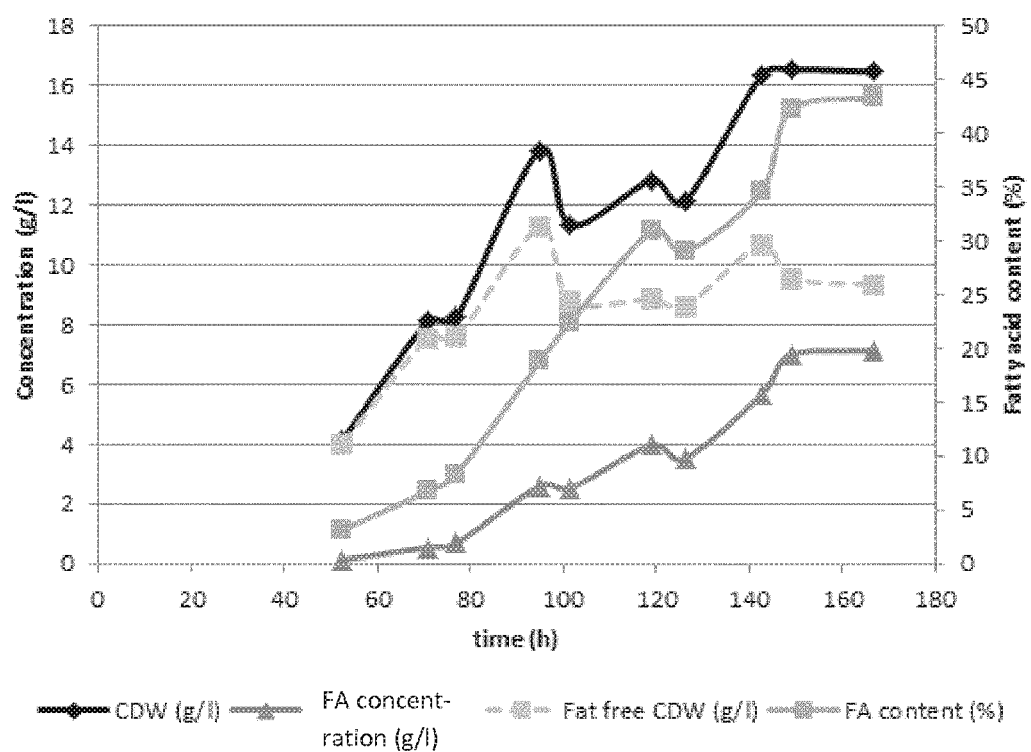
FIG. 1 presents performance (cell dry weigh (CDW) (g/l), fatty acid (FA) concentration (g/l), fat free cell dry weight (CDW) (g/l) and fatty acid (FA) content (%) in microbial biomass) of fed-batch fermentation with *Aspergillus. oryzae* on wheat straw cellulose and hemicellulose hydrolyzates.

In describing the embodiments of the invention specific terminology will be resorted to for the sake of clarity. However, the invention is not intended to be limited to the specific terms so selected, and it is understood that each specific term includes all technical equivalents which operate in a similar manner to accomplish a similar purpose.

This invention deals with the utilization of (ligno)cellulosic materials as a raw material for the production of single cell oils. The single cell oil produced can be used as a raw material for production of biofuels, such as biodiesel, renewable diesel or jet fuel.

Definitions

Microbial Growth Inhibitor

In the context of the present invention the term "microbial inhibitor" or "inhibitory compound" refers here as compounds, derived from lignocellulosic material, i.e. lignocellulose degradation products that can inhibit growth of microorganisms. Such compounds are typically generated in lignocellulose fractionation where lignocellulosic sugars are produced. Such compounds include, but are not limited to phenolic compounds (such as 4-hydroxybenzoic acid, p-coumaric acid, vanillic acid, vanillin, phenol, guaiacol, hydroquinone, catechol, ferulic acid, syringaldehyde, syringic acid), furfural, hydroxymethylfurfural (HMF), organic acids such as (acetic acid, formic acid and levullinic acid) and extractives (caproic acid, caprylic acid, palmitic acid and pelargonic acid). The growth inhibitory effects of these compounds can depend on microorganism and on cultivation conditions. When inhibitory compounds occur in mixes, they can have cumulative effects, i.e. inhibit microbial growth in lower concentrations than without the presence of other inhibitory compound(s).

In the context of the present invention carbohydrates from lignocellulosic biomass does not fall within the definition of microbial inhibitor.

"Optimised levels of fermentation inhibitors" the term refers here to a concentration of inhibitory compounds that allows growth and lipid production by oleaginous microorganisms, but inhibits the growth of contamination non-oleaginous microorganisms.

Aromatic Compounds, Phenolic Compounds

Aromatic hydrocarbon refers here to a compound having a ring structure, formed by covalent linkages between carbon atoms, that contains alternating conjugated double and single bonds in a ring structure. Aromatic hydrocarbon can also refer to a compound having a ring structure, formed by covalent linkages between carbon atoms and non-carbon atoms, that contains alternating conjugated double and single bonds in a ring structure.

The term "phenolic compound" refers here to a compound comprising at least one aromatic hydrocarbon group containing at least one hydroxyl group (—OH) bonded directly to the aromatic hydrocarbon group. In this application the phenolic compound concentration has been measured with colorimetric analysis according to the Folin-Ciocalteu method (Waterhouse, 2002). Such compounds include, but are not limited to phenolic compounds such as p-coumaryl alcohol, coniferyl alcohol, sinapyl alcohol, 4-hydroxyacetophenone, acetovanillone, acetosyringone, 4-hydroxybenzaldehyde, vanillin, syringaldehyde, 4-hydroxybenzoic acid, vanillic acid, syringic acid, p-coumaric acid, ferulic acid, sinapic acid, phenol, guaiacol, syringol, hydroquinone, catechol, 2-methylphenol, 3-methylphenol, 4-methylphenol, 2,6-dimethylphenol, 2,4-dimethylphenol, 4-ethylphenol, 3,4-dihydroxybenzaldehyde, 4-methylguaiacol, 4-vinylphenol, 4-ethyl-2-methylphenol, 4-allylphenol, 3-methoxycatechol, 2,6-dimethoxy-4-methylphenol, vanillyl alcohol, homovanillin, homovanillic acid, 1-(4-hydroxy-3-methoxyphenyl)ethanol, 1-(4-hydroxy-3-methoxyphenyl)allene, vanillic acid methyl ester, 4-ethyl-2,6-dimethoxyphenol, 4-methylcatechol, 4-ethylguaiacol, 4-propylphenol, 4-vinylguaiacol, 4-hydroxybenzyl alcohol, 3-hydroxy-2-methyl-(4H)-pyran-4-one, 3,5-dihydroxy-2-methyl-(4H)-pyran-4-one, 4-propenylphenol, 2,6-dimethoxy-4-propylphenol, dihydroconiferyl alcohol, homosyringaldehyde, 3,5-dimethoxy-4-hydroxybenzyl alcohol, 2,6-dimethoxy-4-propenylphenol, 1-(3,5-dimethoxy-4-hydroxyphenyl)ethanol, coniferyl aldehyde, syringylacetone, syringic acid methyl ester, propiosyringone, syringyl vinyl ketone, dihydrosinapyl alcohol, sinapaldehyde, 2,6-dimethoxyphenol, 1-(4-hydroxyphenyl)ethanol, eugenol, 5-ethylpyrogallol, 4-propylguaiacol, 1,4-dihydroxy-3-methoxybenzene, isoeugenol, 4-hydroxybenzoic acid methyl ester, guaiacylacetone, 2,6-dimethoxy-4-vinylphenol, propiovanillone, guaiacyl vinyl ketone, 4-allyl-2,6-dimethoxyphenol, and including all their possible isomers, oligomeric and/or polymeric lignin, tannins, polyphenols, mixtures of phenolic compounds, covalently linked compounds comprising non-phenolic compounds and phenolic compounds.

The term "concentration of phenolic compounds" is meant the concentration of compounds (typically expressed as g/l) in aqueous solution as measured with the Folin-Ciocalteu method (Waterhouse, 2002)

Lignocellulosic Material

The terms "lignocellulosic biomass" or "lignocellulosic material" is meant to include but is not limited to woody plants or non-woody, herbaceous plants or other materials containing cellulose and/or hemicellulose: Materials can be agricultural residues (such as wheat straw, rice straw, chaff, hulls, corn stover, sugarcane bagasse, sugar cane tops and leaves), dedicated energy crops (such as switchgrass, *Miscanthus*, *Arundo donax*, reed canary grass, willow, water hyacinth, energy cane, energy sorghum), wood materials or residues (including sawmill and pulp and/or paper mill residues or fractions, such as hemicellulose, spent sulphite liquor, waste fibre and/or primary sludge), moss or peat, or municipal paper waste. The term lignocellulosic material comprises also low lignin materials, materials such as macroalgae biomass. In addition, the materials comprise also hemicellulose or cellulose fractions from industrial practises. The term lignocellulosic material encompasses any kind of cellulose fraction. The raw materials or certain fractions, such as hemicellulose and/or cellulose, of raw materials from different origin, plant species, or industrial processes can be mixed together and used as raw materials for cultivating microorganism biomass according to this disclosure. Typically the lignin content in lignocellulose is higher than 5%. Lignocellulosic biomass may also contain starch, e.g. in the case of whole plants Hydrolysis The term "hydrolysis" refers here to depolymerization by addition of water into glycosidic linkages or ester linkages of non-monomeric carbohydrates to sugar oligomers and monomers or carboxylic acids.

Hydrolysate

The terms "hydrolysate" or "hydrolysed material" refers here to material that has undergone hydrolysis.

Lignocellulose Hydrolysate

The term "lignocellulose hydrolysate" refers here to hydrolysis products of lignocellulose or lignocellulosic material comprising cellulose and/or hemicellulose, oligosaccharides, mono- and/or disaccharides, acetic acid, formic acid, other organic acids, furfural, hydroxymethyl furfural, levulinic acid, phenolic compounds, other hydrolysis and/or degradation products formed from lignin, cellulose, hemicellulose and/or other components of lignocellulose, nitrogen compounds originating from proteins, metals and/or non-hydrolyzed or partly hydrolyzed fragments of lignocellulose.

Hydrothermal Treatment

In the context of the present invention the term "hydrothermal treatment" refers to heat treatment of aqueous lignocellulose suspension at temperatures exceeding 50° C. Hydrothermal treatment can be carried out under pressure in a pressurized reactor or at atmospheric pressure in a non-pressurized reactor. The pressure in pressurized reactor may be generated by steam obtained from the water when heated up to boiling point or by added pressurized gas phase. Hydrothermal treatment may be carried out in the presence of a catalyst or in the absence of a catalyst. Hydrothermal treatment in the absence of a catalyst (also referred to as "autohydrolysis" or "AH") to hydrolysis of lignocellulosic biomass without added catalyst when aqueous suspension of lignocellulosic biomass is subjected to hydrothermal treatment at temperatures exceeding 120° C. under pressure.

"Autohydrolyzed straw" refers here to solid fraction that has been obtained after autohydrolysis. Autohydrolysed straw may have been subjected to washing.

Steam Explosion

In the context of the present invention the term "steam explosion" refers to a treatment, where the material is heated by a high pressure steam (at temperatures between 110° C. and 250° C., typically 140-230° C.) under a pressure with or without the addition of chemicals (such as acids) and the material is held at the temperature for a certain time after which the pressure is released causing an explosive decompression of the material. In this context, steam explosion is applied to lignocellulosic materials, and it typically results in a rupture of the lignocellulose fibers rigid structure, i.e. defibrillation of the cellulose fibre bundles.

Delignification Treatment

"Delignification treatment" refers here to a treatment that removes non-carbohydrate material such as lignin from lignocellulosic biomass. Delignification treatment also refers to a treatment that removes both non-carbohydrate and carbohydrate material as a mixture from lignocellulosic biomass.

Alkaline Delignification Agent

In the context of the present invention the term "alkaline delignification agent" refers to a chemical compound or a mixture of chemical compounds that when added to water give solutions with a hydrogen ion activity lower than that of pure water, i.e., a pH higher than 7.0. Alkaline delignification agent can be selected from a group of compounds comprising but not limited to hydroxides such as LiOH (lithium hydroxide), NaOH (sodium hydroxide), KOH (potassium hydroxide), $Ca(OH)_2$ (calcium hydroxide), $NH_4OH$ (ammonium hydroxide), or compounds that can form hydroxide ions in water such as $NH_3$ (ammonia) in liquid or gaseous state, carbonates such as $HCO_3-$ (bicarbonate ion), $Li_2CO_3$ (lithium carbonate), $Na_2CO_3$ (sodium carbonate), $K_2CO_3$ (potassium carbonate), sulfides such as $Na_2S$ (sodium sulfide), and the corresponding hydrates.

Enzymatic Hydrolysis

In the context of the present invention the term "enzymatic hydrolysis" refers to enzymatic treatment of the lignocellulosic material comprising cellulose and/or hemicellulose, oligosaccharides, where enzymes facilitates the hydrolysis of the cellulose and/or hemicellulose, oligosaccharides to obtain mono- and/or disaccharides. Typically the enzymatic hydrolysis treatment of the lignocellulosic material is conducted by subjecting the lignocellulosic material to a mixture of enzymes in the presence of water or a buffer. The mixture of enzymes typically consists of, but is not limited to 1,4-β-glucanases (endoglucanaces and exoglucanases, or endocellulases and exocellulases), 1,4β-glucosidases (cellobiases) and hemicellulose-degrading enzymes (hemicellulases, xylanases, arabinases etc.).

Fraction of Lignocellulosic Biomass

"Fraction of lignocellulosic" biomass refers here any fraction that has been derived from lignocellulosic biomass and may be thus lignin free.

Microbial Lipid or Lipid

In the context of the present invention "microbial lipid", "lipid" or "intracellular lipid" refers to a fatty substance, whose molecule generally contains, as a part, an aliphatic hydrocarbon chain, which dissolves in nonpolar organic solvents but is poorly soluble in water. Lipids are an essential group of large molecules in living cells. Lipids are, for example, fats, oils, waxes, wax esters, sterols, terpenoids, isoprenoids, carotenoids, polyhydroxyalkanoates, nucleic acids, fatty acids, fatty alcohols, fatty aldehydes, fatty acid esters, phospholipids, glycolipids, sphingolipids and acylglycerols, such as triacylglycerols, diacylglycerols, or monoacylglycerols.

Preferred lipids in the present invention are fats, oils, waxes, acylglycerols and fatty acids and their derivatives, in particular triacylglycerols and wax esters. In the context of the present invention the lipids are synthesized by and accumulated in microbes (intracellular lipids).

In connection of this invention single cell oil is used as synonym for lipids and fat.

The term "acyglycerol" refers to an ester of glycerol and fatty acids. Acylglycerols occur naturally as fats and fatty oils. Examples of acylglycerols include triacylglycerols (TAGs, triglycerides), diacylglycerols (diglycerides) and monoacylglycerols (monoglycerides).

Sugar

In the context of the present invention the term "sugar" refers here to oligomeric, dimeric and monomeric carbohydrates. Particularly, in this application the term sugar refers to water soluble oligomeric, dimeric and monomeric carbohydrates derived from lignocellulosic materials. By the term "polymeric sugars" is meant carbohydrates that are in polymeric form and not typically soluble in water.

Sugar Yield

In the context of the present invention the term "sugar yield" refers here to the yield of oligomeric, dimeric and monomeric carbohydrates from particular materials. Particularly, in this application the term sugar yield refers to the yield of water soluble oligomeric, dimeric and monomeric carbohydrates derived from lignocellulosic materials.

Single Cell Oil Production Process

"Single cell oil production process" refers here to a process, comprising steps of forming or allowing the growth of a lipid synthesizing microorganism and allowing the thus obtained organism mass to produce and/or store (accumulate) lipid, recovering the cells from the liquid phase, and extracting or recovering the lipids from the cells. In certain cases, single cell oil can be also extracellular such as excreted or liberated from cells in culture medium during or after cultivation.

Aerobic Cultivation

The term "aerobic cultivation" or "aerobic fermentation" refers to a cultivation where the microorganism utilizes oxygen as terminal electron acceptor for energy generation (i.e. microorganism uses aerobic respiration). Typically in bioreactors, aerobic cultivation is performed by adding oxygen or a gas mixture containing oxygen (typically air), i.e. bioreactor is aerated. When microorganisms uses aerobic respiration in cultivation, it can be referred as "cultivation under aerobic conditions". Typically this occurs in aerated bioreactors.

Aseptic Operation

The term "aseptic operation" refers here operation where microorganism cultivation systems (e.g. fermenter) have been sterilized prior to cultivation, and where operation is performed in a way which prevents contamination (i.e. growth of non-desired microorganisms) of cultivation systems, e.g. by using antimicrobial agents not derived from lignocellulose pre-treatment. "Non-aseptic operation" refers operation performed otherwise than "aseptic operation"

Oleaginous Microbe or Oil Producing Microorganism

The oleaginous microbe (also refer to as oil producing organisms) used in the present invention are selected from the group of bacteria, cyanobacteria, fungi such as yeasts and filamentous fungi, archaea or microalgae. The microorganisms can readily accumulate lipids or have been genetically modified to accumulate lipids or to improve accumulation of lipids.

Preferably organisms that are capable of utilizing C6 and C5 sugars are used. Preferably organisms are yeast, filamentous fungi or bacteria.

In the context of the present invention, the oleaginous microorganism (oleaginous microbe) refers to a microorganism which is capable of accumulating intercellular lipids such that the lipids mounts at least 15% (w/w) of the total biomass (per cell dry weight) of the microbe when it is cultivated under suitable conditions. In a preferred embodiment, the oleaginous microbe is capable of accumulating at least 20% (w/w) of the total biomass of the microbe (per cell dry weight).

Preferred microorganism strains for the purposes of the present invention include, but are not limited to, the species and genera listed below:

According to one embodiment of the invention, the first microbe is an oleaginous microbe capable of utilizing sugars derived from lignocellulosic materials. Preferably, oleaginous organisms are capable of utilizing C6 sugars (six carbon sugars, such as glucose, mannose and galactose) and C5 sugars (such as xylose and arabinose) in lignocellulosic hydrolysates. According to one embodiment of the invention, the oleaginous organism is capable of utilizing polymeric or oligomeric carbohydrates in lignocellulose or fractions thereof.

Preferred (filamentous) fungal strains are from species from genera *Aspergillus* such as *Aspergillus oryzae*, *Mortierella* such as *Mortierella isabellina*, *Chaetomium*, *Claviceps*, *Cladosporidium*, *Cunninghamella*, *Emericella*, *Fusarium*, *Glomus*, *Mucor*, *Pseudozyma*, *Pythium*, *Rhizopus*, such as *Rhizopus oryzae*, *Tremella*, *Zygorhynchus*, *Humicola*, *Cladosporium*, *Malbranchea*, *Umbelopsis* such as *Umbelopsis isabellina* and *Ustilago*. Most preferred fungal species are from genera *Aspergillus* and/or *Mortierella*. Preferred fungi are those fungi capable of producing effectively lipids.

Preferred yeast strains are those belonging to species from genera, *Geotrichum, Deparyomyces, Pachysolen, Galactomyces, Hansenula, Leucosporidium, Sporobolomyces, Sporidiobolus, Waltomyces, Cryptococcus*, such as *Cryptococcus curvatus, Rhodosporidium*, such as *Rhodosporidium toruloides* or *Rhodosporidium fluviale, Rhodotorula*, such as *Rhodotorula glutinis, Yarrowia*, such as *Yarrowia lipolytica, Candida* such as *Candida curvata, Lipomyces* such as *Lipomyces starkeyi* and *Trichosporon* such as *Trichosporon cutaneum* or *Trichosporon pullulans*. Most preferred yeasts are from genera *Lipomyces, Rhodosporidium* and *Cryptococcus*. Preferred yeasts are those yeasts capable of producing effectively lipids.

Preferred bacteria are those belonging to the species from genera *Rhodococcus, Acinetobacter* and *Streptomyces*. Preferred bacteria are those bacteria capable of producing effectively lipids.

Most preferred algae are microalgae, such as microalgae species from genera comprising, *Brachiomonas, Crypthecodinium, Chlorella, Dunaliella, Hantzschia, Nannochloris, Nannochloropsis, Nitzschia, Prototheca, Scenedesmus, Schizochytrium, Traustrochytrium* and *Ulkenia*. Preferred microalgae are those microalgae capable of growing heterotrophically and producing effectively lipids. The organisms belonging to the genera *Schizochytrium, Thraustochytrium* and *Crypthecodinium* and *Ulkenia* are sometimes called as marine fungi.

According to another embodiment of the invention, the carbohydrates from lignocellulosic biomass are in mainly monomeric form and organisms not capable of utilizing oligomeric or polymeric carbohydrates are used for single cell oil production.

Such oil producing organisms are selected from the group of bacteria, cyanobacteria, fungi such as yeasts and filamentous fungi, archaea or microalgae. The microorganisms can readily accumulate lipids or have been genetically modified to accumulate lipids or to improve accumulation of lipids.

Lipid Containing Single-Cell Mass

"Lipid-containing single-cell mass" stands for a single-cell mass and cellular mycelium with a lipid content of at least preferably at least 10%, preferably at least 15% (w/w) or more of dry matter of the microorganism biomass.

Lipid Recovery

"Oil recovery" or "Lipid recovery" or "recovering lipid from an oleaginous microbe" refers to a process, in which the lipid (intracellular lipid) is recovered by mechanical, chemical, thermomechanical or autocatalytic methods or by a combination of these methods from the microorganism cells. Alternatively, "oil recovery" can mean the recovery of extracellularly produced lipids from the cultivation (fermentation) broth.

Residual Cell Mass

In the context of the present invention "residual cell mass" refers to a solid, semi-solid or flowing material fraction, which contains microorganisms treated for the recovery of intracellular lipids Biofuel In the context of the present invention "biofuel" refers to solid, liquid or gaseous fuel mainly derived from biomass or biowaste and is different from fossil fuels, which are derived from the organic remains of prehistoric plants and animals.

According to EU directive 2003/30/EU "biodiesel" refers to a methyl-ester produced from vegetable oil or animal oil, of diesel quality to be used as biofuel. More broadly, biodiesel refers to long-chain alkyl esters, such as methyl, ethyl or propyl-esters, from vegetable oil or animal oil of diesel quality. Biodiesel can also be produced from microorganism lipids, whereby microorganism lipid can originate from a bacterium, a fungus (yeast or a filamentous fungus), an algae or another microorganism.

Renewable Diesel

"Renewable diesel" refers to a fuel which is produced by a hydrogen treatment of lipids of an animal, vegetable or microorganism origin, or their mixtures, whereby microorganism lipid can originate from a bacterium, a fungus (yeast or a filamentous fungus), an algae or another microorganism. Renewable diesel can be produced also from waxes derived from biomass by gasification and Fischer-Tropsch synthesis. Optionally, in addition to hydrogen treatment, isomerization or other processing steps can be performed. Renewable diesel process can also be used to produce jet fuel and/or gasoline. The production of renewable diesel has been described in patent publications EP 1396531, EP1398364, EP 1741767 and EP1741768.

Biodiesel or renewable diesel may be blended with fossil fuels. Suitable additives, such as preservatives and antioxidants may be added to the fuel product.

Lubricant

"Lubricant" refers to a substance, such as grease, lipid or oil that reduces friction when applied as a surface coating to moving parts. Two other main functions of a lubricant are heat removal and to dissolve impurities. Applications of lubricants include, but are not limited to uses in internal combustion engines as engine oils, additives in fuels, in oil-driven devices such as pumps and hydraulic equipment, or in different types of bearings. Typically lubricants contain 75-100% base oil and the rest is additives. Suitable additives are for example detergents, storage stabilizers, antioxidants, corrosion inhibitors, dehazers, demulsifiers, antifoaming agents, co-solvents, and lubricity additives (see for example U.S. Pat. No. 7,691,792). Base oil for lubricant can originate from mineral oil, vegetable oil, animal oil or from a bacterium, fungi (yeast or a filamentous fungus), an algae or another microorganism. Base oil can also originate from waxes derived from biomass by gasification and Fischer-Tropsch synthesis. Viscosity index is used to characterise base oil. Typically high viscosity index is preferred.

The lipids produced according with the method described in this invention can be used as feedstock for the production of biodiesel, renewable diesel, jet fuel or gasoline. Biodiesel consists of fatty acid methyl esters, and is typically produced by transesterification. In transesterification, the acylglycerols are converted to long-chain fatty acid alkyl (methyl, ethyl or propyl) esters. Renewable diesel refers to fuel which is produced by hydrogen treatment (hydrogen deoxygenation, hydrogenation or hydroprocessing) of lipids. In hydrogen treatment, acylglycerols are converted to corresponding alkanes (paraffins). The alkanes (paraffins) can be further modified by isomerization or by other process alternatives. Renewable diesel process can also be used to produce jet fuel and/or gasoline. In addition, cracking of lipids can be performed to produce biofuels. Further, lipids can be used as biofuels directly in certain applications.

Lipids produced with the method can also be used as base oils for lubricants (lubrication oils) or as a starting material for production of base oils for lubricants Dry Matter "DM" or "dry weight" refers here to dry matter and is a measurement of the mass of a material when it has been subjected to a treatment that essentially removes water from the material (i.e. material is completely dried).

Consistency

"Consistency" refers here to the ratio of dry weight of solids to total weight of suspension.

Method of Producing a Microbial Lipid

In a first aspect of the present invention a method for producing lipids, comprising the following steps
  (i) providing a cultivation medium comprising a lignocellulosic hydrolysate,
  (ii) providing a fermentation broth by inoculating the cultivation medium of (i) with a first microbe, where said first microbe is an oleaginous microbe,
  (iii) incubating said medium inoculated with said first microbe allowing lipids to accumulate,
wherein said fermentation broth comprises at least one microbial growth inhibitor, and wherein said first microbe is tolerant to said microbial growth inhibitor(s), wherein said incubation is conducted under aerobic conditions.

The method of the invention is also referred to as a single cell oil production process. The method of the present invention may be part of process for productions of biofuels as described herein, where the oil or at least part of the oil provided in the form of microbial oil by the method described herein.

According to preferred embodiment of the invention the cultivation medium comprises lignocellulosic sugars derived from cellulose and/or hemicellulose. According to the invention, both hemicellulose and/or cellulose fractions of lignocellulosic biomass are used as raw materials for microbial oil production (single cell oil) in the same process (bioreactor system). The process uses preferably oleaginous microbe that are capable of utilizing both C6 (e.g. glucose, mannose, galactose) and C5 (e.g. xylose, arabinose) sugars.

According to another embodiment of the invention, the cultivation medium comprises hemicellulosic sugars derived from lignocellulose. According to yet another embodiment of the invention, the hemicellulosic sugars are at least partly in oligomeric form when fed to a single cell oil production process.

According to one, preferred embodiment of the invention, hemicellulosic fraction is first separated from lignocellulosic material. The separation can be performed with any method, preferably by hydrothermal treatment, autohydrolysis and/or steam explosion with or without addition of acids resulting in a liquid fraction containing hemicellulosic sugars and a solid fraction containing cellulose and lignin. The liquid fraction typically contains compounds that inhibit growth of microorganisms, compounds which are produced in the lignocellulose fractionation process. These compounds are degradation production of lignocellulose, such as lignin and sugars, and comprise phenolic compounds, furan compounds (furfural and derivates thereof) and organic acids (mainly acetic acid, formic acid). Also the solid fraction containing cellulose and lignin contains inhibitory compounds, depending on the extent of washing. According to the invention, the cultivation medium comprises a liquid stream from fractionation step consisting hemicellulose sugars can be fed to cultivation without enzymatic hydrolysis of sugar oligomers, or alternatively hemicellulose stream containing sugar oligomers can be fed to enzymatic hydrolysis to produce sugar monomers prior to be used in microbial cultivation. According to invention, the solid cellulose-lignin fraction is fed to enzymatic treatment to dissolve cellulose and residual hemicellulose (not dissolved in the fractionation step) to sugar monomers for microbial oil production.

The lipid typically accumulate as intracellular lips within the oleaginous microbe (referred to as the first microbe), however the microbial lipid may also be secreted or at least partly secreted to the fermentation broth from which it may be recovered. Thus, in one embodiment, the method further comprises a step of recovering the accumulated lipid from said first microbe (oleaginous microbe). In another embodiment, the lipid is recovered from the fermentation broth. Lipid recovery may be carried out in various ways as discussed herein.

The incubation (cultivation) step (iii) may be performed as any suitable aerobic cultivation including batch, fed batch or continuous cultivation.

Where cultivation medium, the fermenter (bioreactor) or systems connected to with the fermenters has not been sterilized cultures of contaminating microbes may establish. It follows that where such contaminating microbes are not oleaginous microbes they may compete with the oleaginious microbes on the available substrate and thereby reduce the lipid yield in the production.

These contaminating microbes (referred to a second microbe) are unwanted and should be avoided or suppressed in the system. By the introduction of a microbial inhibitor to which the oleaginous microbe is tolerant, the establishment of contaminating microbes (second microbe) avoided or suppressed in the system, where the latter is sensitive or at least less tolerant to said microbial inhibitor.

Where the lignocellulosic hydrolysate has hot been sterilized, it will typically contain one or more species of non-oleaginous microbes, which are therefore unwanted in the cultivation and falls within the definition of the second microbe. Thus, in one embodiment said second microbe is a non-oleaginous microbe.

In one embodiment of the present invention, the second (non-oleaginous microbes) is introduced or has established in the production system, e.g. the fermenter and thus will contaminate the fermentation broth. Thus, in one embodiment of the invention, the fermentation broth further comprises a second microbe, which is intolerant to said at least one microbial growth inhibitor. Alternatively the second microbe is introduced during preparation for the cultivation, for example with the lignocellulosic hydrolysate. Accordingly, in a further embodiment, the second microbe is present in the cultivation medium provided in step (i) or contaminated the fermentation broth at step (ii) or (iii) or present in the bioreactor.

The object of the present invention is therefore to avoid that these contaminating microbes (referred to a second microbes) establish in the system. The is accomplished by introducing at least one microbial growth inhibitor to which the oleaginous microbe (first microbe) is tolerant or at least more tolerant and the contaminating microbes (second microbe) is intolerant or at least less tolerant to than the first microbe.

It is evident from the above description that if the first microbe is "tolerant" to a microbial growth inhibitor, it means that said first microbe (the oil producing microbe", is able to proliferate and/or produce oil even in the presence of said microbial growth inhibitor. Furthermore, it is evident that "intolerant" in the context of e.g. a second (contaminating) microbe, means that said second microbe will be inhibited in its growth, such as prevented from proliferating in a media which comprises a sufficient concentration of said microbial growth inhibitor.

From the methods and data described in the example section, it is also evident to the skilled person how to test the ability of any oil producing microbe to proliferate and/or produce oil at a reasonable level in the presence of a microbial growth inhibitor. And further, it is also evident for the skilled person, based on the methods and data presented in the examples how to test any second (potentially contaminating) microbe for how intolerant it is to said microbial growth inhibitor, and thereby which exact concentration of said microbial growth inhibitor is needed in the media to inhibit proliferation (growth) of said second microbe. Therefore, knowledge and methods are available to test the ability of a first (oil producing microbe) to outgrow contaminating second microbes under conditions where the medium comprises a microbial growth inhibitor, in amounts as defined in this application, or as defined by experiments such as those described in the examples section.

Tolerant therefore means that the tolerant microbe is able to outgrow the intolerant microbe in the presence of the microbial growth inhibitor.

The range of tolerance is thus the concentration range of a certain microbial inhibitor within which a particular first microbe is capable of proliferating and producing oil at a level which does not differ more than 50% from the level of proliferation or production when the microbial growth inhibitor is not present in the media.

As can be seen from the methods and data presented in the examples, the range of tolerance can easily be determined using these methods. Likewise, "outside the range of tolerance" of the second microbe simply means that using the methods described in the examples, the skilled person may determine if a concentration of a microbial growth inhibitor is outside the range of tolerance of a certain second microbe. Being outside the range of tolerance means that such concentration of a microbial growth inhibitor inhibits growth or proliferation of said second microbe by at least 20%, such as at least 30%, or 40%, or at least 50% when compared to the same media without said microbial growth inhibitor.

Monitoring the concentration of the microbial growth inhibitor and subsequently adjusting the concentration of said microbial growth inhibitor in a reactor during growth or production may be needed, as some microorganisms will cause either an increase or a decrease in the concentrations of e.g. phenolic compounds in the medium. Therefore, "adjusting the concentration" means that the concentration will be adjusted accordingly to still be within the desired range which is within the tolerable range for the first microbe and without the tolerable range for the second microbe.

The present inventors have discovered that compounds (such as phenolic compounds) present in the lignocellulosic hydrolysate may function as microbial inhibitors in the method of the present invention. Thus, in one embodiment of the present invention, said at least one microbial growth inhibitor is present in the cultivation medium provided in step (i), such as in the lignocellulosic hydrolysate of the cultivation medium. The microbial growth inhibitor compounds can be also added during the cultivation along with the lignocellulosic hydrolysate, such as in fed-batch cultivation.

According to the present invention the oleaginous microbe (first microbe) is tolerant or at least partly tolerant to the microbial inhibitor present during the cultivation. The second microbe, on the other hand is intolerant to the microbial inhibitor or at least less tolerant to the microbial inhibitor than the first microbe, which allows the concentration of the microbial inhibitor to be adjusted such that the conditions of the oleaginous microbe are favourable over that of the second microbe.

In one embodiment of the present invention, said at least one microbial growth inhibitor is present in said fermentation broth at a concentration within the range of tolerance of said first microbe and outside the range of tolerance of said second microbe. In a further embodiment, the method further comprising a step of adding said at least one microbial growth inhibitor or adjusting the concentration of said at least one microbial growth inhibitor in the fermentation broth.

The method of the invention enables efficient microbial oil production without the need of sterilizing the cultivation medium prior to make the fermentation broth by inoculating it with the oleaginous microbe. Thus in one embodiment of the present invention, the method is not performed under aseptic conditions. In a further embodiment, the cultivation medium comprising lignocellulosic hydrolysate provided in step (i) has not been sterilized. In other words, in one embodiment the method of the invention is carried out as a non-aseptic process (non-aseptic operation).

The sterilization of bioreactors and cultivation medium also requires more energy and more expensive reactor design compared to bioreactor systems that does not include sterilization. Thus, avoiding the sterilization can improve the cost efficiency of cultivation by allowing less expensive operation and lower investment costs.

The present inventors has discovered that in particular phenolic compounds such as phenolic compound present in the lignocellulosic hydrolysate following as a process of the fractionation of the lignocellulosic material is particular useful as microbial inhibitor in the method of the present invention. The advantage of using this class of inhibitors is that it is introduced with the lignocellulosic hydrolysate and the concentration may be adjusted to fall within the window of tolerance of the oleaginous microbe (first microbe) and outside the window of tolerance of the second microbe (non-oleaginous microbe) in case the latter is partly tolerant to the microbial inhibitor.

The method of the present invention preferably uses oleaginous microbes that are highly tolerant to lignocellulose-based inhibitors, which provides a larger window for adjusting the level of the microbial inhibitor in the fermentation broth.

The inhibitor includes, but not limited to phenolic compounds, organic acids, furfural and hydroxymethylfurfural, which are present in in hemicellulose and/or cellulose fractions. The concentration may be adjusted into reach a level where the growth of contaminating microorganisms (non-oleaginous microbe) is suppressed without affecting or at least significantly affecting the growth of the oleaginous microbe. It follows that since the method preferable use microbial inhibitors present in the lignocellulosic hydrolysate then the hydrolysate has not been subjected to a step of removing the microbial inhibitors from the hydrolysate. Thus in one embodiment of the present invention, the cultivation medium comprising a lignocellulosic hydrolysate provided in step (i) has not been subjected to a process of detoxification to remove said at least one growth inhibitor.

In one embodiment of the present invention, the at least one microbial growth inhibitor is the group of phenolic compound, such as the total group of phenolic compounds present in the in the lignocellulosic hydrolysate (measured as total phenols per volume, e.g. g/l). In a further embodiment the level of said phenolic compounds in said fermentation broth is at least 1 g/l. The concentration may be reached by adjusting the concentration of the cultivation medium to reach the desired concentration in the fermentation broth. The phenolic compounds are analysed with Folin-Ciocalteu method (Waterhouse, 2002), which indicates the total amount of phenolic compounds in a liquid.

In a further embodiment, the level of said phenolic compounds in said fermentation broth is in the range of 1 g/l to 7 g/l or above (growth medium). According to one embodiment of the invention, the concentration of phenolic compounds in the fermentation broth is between 7 and 10 g/l, according to another embodiment the concentration is between 10 and 20 g/l, and according to yet another embodiment, the concentration of phenolic compounds is between 20 and 50 g/l. In yet a further embodiment, the level of said phenolic compounds in said fermentation broth is within the range of 1 g/l to 5 g/l, preferably within the range of 1 g/l to 3 g/l.

The content of the microbial inhibitor in the lignocellulosic hydrolysate (hemicellulose and cellulose fractions) and/or in the fermentation broth can be adjusted in various ways to reach the desired level in the fermentation broth.

The inhibitor concentration in liquid hemicellulose stream can be adjusted by changing the conditions (such as temperature, delay (retention time), pH, dry matter content), e.g. the severity factor, in lignocellulose fractionation process step used for (at least partial) hemicellulose liquefaction, such as in hydrothermal treatment, autohydrolysis and/or steam explosion with or without addition of acids. By chancing the conditions in lignocellulose fractionation, the inhibitory compounds can be adjusted to result in certain level of inhibitory compounds in liquid stream containing hemicellulose.

Alternatively, the concentration of microbial inhibitors in hemicellulosic sugar stream is adjusted by purification of the hemicellulose stream by any known methods, including but not limited to adsorption, absorption, filtration, stripping, liming, evaporation, extraction or enzymatic treatment.

Typically, the sugar stream containing mainly hemicellulosic sugars (C5-rich stream) derived from the lignocellulose fractionation step resulting in hemicellulose liquefaction (at least partially) contain higher amounts of inhibitory compounds, such as phenolic compounds, organic acids (such as acetic acid and formic acid), furfural and/or hydroxymethylfurfural than sugar stream (C6-rich stream) from enzymatic hydrolysis of solid fraction containing cellulose and lignin.

The microbial inhibitor concentration in the sugar stream used in cultivation may be adjusted by mixing the hemicellulosic sugar steam (C5-rich stream) and cellulosic sugar stream (C6-rich stream). The mixing of the hemicellulosic and cellulosic sugar stream can be done in any proportion to achieve the appropriate concentration of inhibitors in the cultivation that allows the growth of oil producing organisms but prevents or significantly inhibits the growth of contaminating organisms (not capable of efficient oil production).

Treatments to liquids derived from lignocellulose pretreatment can be performed that also result in the increased concentration of inhibitors or increase of concentration of certain inhibitors and removal of other inhibitors which can be advantageous. E.g. evaporation of liquid from pre-treatment containing hemicellulosic carbohydrates can result in increased concentration of non-volatile inhibitors (such as phenolic compounds) and decreased concentration of volatile inhibitors such as furfural, acetic acid and formic acid. Thus, part of the volatile compounds such as furfural, may be removed during the concentration of carbohydrates Typically, in single cell oil production concentrated sugars are used. In concentration of sugar streams from lignocellulose fractionation and enzymatic hydrolysis, typically evaporation is used. Evaporation results in the concentration of non-volatile compounds, e.g. phenolic compounds, in the sugar concentrate. Preferably, organisms are used in single cell oil production which tolerate high concentrations of phenolic compounds.

According to one, preferred embodiment of the invention sugar streams from lignocellulose fractionation containing hemicellulose and cellulose are concentrated prior to be fed to single cell oil production process, but no other purification step is performed. Thus the optimal amount of inhibitors that allows growth of oleaginous microorganisms but inhibits the growth of contaminating non-oleaginous microorganisms is achieved by adjusting the conditions in lignocellulose fractionation, by evaporation of lignocellulosic sugar streams and by mixing the hemicellulose sugar rich-stream (C5-syrup) and cellulose sugar rich steam (C6-syrup) in fermentation broth.

The enzymatic treatment has long retention time (typically 1 to 3 days) and thus it is prone to microbial contamination causing sugar loss and problems in microbial oil production (aerobic fermentation). According to one, preferred embodiment of the invention, the cellulose+lignin fraction from fractionation step which results in at least partial hemicellulose liquefaction is washed only to such extent that it allows enzymatic treatment but inhibits the growth of contaminating microorganisms in enzymatic hydrolysis and thus decrease the sugar losses.

The amount of inhibitory compounds in the solid fraction from lignocellulose fractionation containing cellulose can be adjusted by the extent of washing the solid cellulose fraction prior to enzymatic hydrolysis, or by changing the process conditions (such as temperature, delay (retention time), pH), in lignocellulosic fractionation process producing the solid cellulose and lignin fraction.

Lignocellulosic Hydrolysate Used by the Method of the Invention

The lignocellulose hydrolysate used by the method of the present invention is a hydrolysis product of lignocellulose or lignocellulosic material. The lignocellulose hydrolysate may be obtained by one or more treatments of the lignocellulose or lignocellulosic material including hydrolysis (hydrothermal treatment and/or autohydrolysis), steam explosion with or without addition of acids, one or more step of delignification, for example delignification using an alkaline delignification agent.

The lignocellulose hydrolysate used by the method of the invention may be a product of any lignocellulose fractionation method where the hemicelluloses are is at least partly dissolved.

In one embodiment the lignocellulose hydrolysate is obtained by treating the lignocellulose with autohydrolysis as a first step. The autohydrolysis is typically performed at 5-40% dry matter content, at temperatures between 140 and 240 C for 1-120 min without addition of acidic compounds resulting in dissolving of 5 to 40% of dry matter content in lignocellulosic material including hemicellulosic carbohydrates. Typically hot water extraction dissolves from 30 to 100% of hemicellulosic carbohydrates from lignocellulosic material, preferably more >50%, more preferably >70%, more preferably >80%, even more preferably >90%. The dissolved hemicellulose carbohydrates are at least partly in oligomeric form. More typically, the autohydrolysis is performed at 10-30% dry matter content at 160-220 C, depending on the lignocellulosic raw material. After autohydrolysis, the solid and liquid phases are separated by any method, such as filtration, e.g. pressure filtration, or by a screw press. The solid fraction may be washed to remove dissolved hemicellulose from solid phase.

According to another embodiment of the invention, the lignocellulose hydrolysate is a product of treating the lignocellulose with steam or steam explosion with or without addition of acidic compounds, in general at temperatures between 110 and 250° C., more typically at temperatures between 140 and 230° C. The treatment results in a dissolving of hemicellulosic carbohydrates. Optionally, the solid material from steam explosion is washed to recover dissolved hemicellulosic carbohydrates.

According to yet another embodiment of the invention, the lignocellulose hydrolysate is a product of treating the lignocellulose with ammonium to dissolve hemicellulosic carbohydrates containing oligomers According to one embodiment of the invention, ammonium fibre expansion (AFEX) or ammonia recycle percolation is used with temperature between 60 C and 220° C.

During the treatment of lignocellulosic material, other organic compounds than carbohydrates, such as phenolic compounds (such as 4-hydroxybenzoic acid, p-coumaric acid, vanillic acid, vanillin, phenol, guaiacol, hydroquinone, catechol, ferulic acid, syringaldehyde, syringic acid), furfural, hydroxymethylfurfural (HMF), acetic acid, formic acid and levullinic acid are typically formed and released in treatment and dissolved in liquid phase along with hemicellulosic carbohydrates. In addition, extractives such as caproic acid, caprylic acid, palmitic acid and pelargonic acid may be released.

Phenolic compounds, furfural, hydroxymethylfurfural, acetic acid and formic acid are typically inhibitory to microbial growth. The concentrations of the compounds that cause growth inhibition are dependent on the microorganism. Some oil producing microorganisms, preferably fungi, more preferably filamentous fungi, are highly tolerant to the inhibitory compounds, such as phenolic compounds, furfural, HMF, acetic acid and formic acid, formed in lignocellulose pre-treatment (i.e. hydrolysis, fractionation).

As mention herein the microbial inhibitors generated during the fractionation of the lignocellulosic material to obtain the lignocellulose hydrolysate is particular useful as microbial inhibitors in the method of the present invention.

The utilization of oleaginous production organisms that are highly tolerant to these inhibitory compounds is favorable since it can decrease the need and complexity of unit operations for the removal of inhibitors and in addition decrease or prevent the growth of contaminating microorganisms in aerobic fermentation process in single cell oil production.

First Microbe

In one step of the method, the cultivation medium comprising a lignocellulosic hydrolysate is inoculated with a first microbe, which is a lipid producing microbe (oleaginous microbe). In one embodiment of the present invention, the first microbe (oleaginous microbe) is selected from the list consisting of filamentous fungi, yeast, bacteria and algae or bacteria. Preferably organisms that are capable of utilizing C6 and C5 sugars are used.

The oleaginous microbe may lipid production by nature or the oleaginous microbe may have obtained by genetic modification, which increases the intracellular lipid production and the microbe capacity to accumulate intracellular lipids.

In the context of the present invention, the first microbe (the oleaginous microbe) refers to a microorganism which is capable of accumulating intercellular lipids such that the lipids mounts at least 15% (w/w) of the total biomass (per cell dry weight) of the microbe when it is cultivated under suitable conditions. Thus in one embodiment of the present invention, said first microbe (oleaginous microbe) is capable of producing and accumulating more than 15% of its weight as lipid (per cell dry weight). In a preferred embodiment, the first microbe (oleaginous microbe) is capable of accumulating at least 20% (w/w) of the total biomass of the microbe (per cell dry weight).

It follows that microbes that does not fall within the above definition with regard to their capacity to accumulate intercellular lipids are regarded as non-oleaginous microbe and therefore unwanted during the incubation. In the context of the present invention, the second microbe refers to a non-oleaginous microbe, i.e. the second microbe capability of accumulating intercellular lipids is below 15% (w/w) of the total biomass (per cell dry weight) when it is cultivated under suitable conditions.

In one embodiment of the present invention the first microbe (oleaginous microbe) is selected from the group consisting of *Mortierella, Aspergillus, Lipomyces, Rhodosporidium* and *Cryptococcus*. The inventors have discovered that species of these genera are particular tolerant to microbial inhibitor present in the lignocellulosic hydrolysate, such as the phenolic compounds discussed herein.

Non-oleaginous microbes (second microbe) include non-oleaginous bacteria including but not limited to *Bacillus* spp. and *Pseudomonas* spp. Thus in one embodiment of the present invention the second microbe is selected from the group consisting of *Bacillus* spp such as *Bacillus subtilis.*, *Pseudomonas* spp. such as *Pseudomonas flourescens*. The inventors have discovered that these non-oleaginous microbes are intolerant to microbial inhibitors present in lignocellulosic hydrolysate, in particular the phenolic compounds of the lignocellulosic hydrolysate.

According another embodiment of the invention, the non-oleaginous second microbe selected from is non-oleaginous yeasts, non-oleaginous filamentous fungi. or non-oleaginous microalgae It follows that where the second microbe (non-oleaginous microbes) is intolerant to microbial inhibitors in the form of phenolic compounds of the lignocellulosic hydrolysate then the oleaginous microbes (first microbe) is preferably selected from the oleaginous microbes, which are particular tolerant to the phenolic compounds present in the lignocellulosic hydrolysate.

Thus, in one embodiment of the present invention the first microbe (oleaginous microbe) is selected from the group consisting of *Mortierella, Aspergillus, Lipomyces, Rhodosporidium* and *Cryptococcus* and the at least one microbial growth inhibitor is the group of phenolic compound, such as the total group of phenolic compounds present in the in the lignocellulosic hydrolysate (measured as total phenol concentration per volume of fermentation broth, e.g. as g/l), and preferably the level of said phenolic compounds in said fermentation broth is at least 1 g/l, such as within the range of 1 g/l to 7 g/l or above (growth medium). In yet a further embodiment, the level of said phenolic compounds in said fermentation broth is within the range of 1 g/l to 5 g/l, preferably within the range of 1 g/l to 3 g/l. According to one embodiment of the invention, the concentration of phenolic compounds in the fermentation broth is between 7 and 10 g/l, according to another embodiment the concentration is between 10 and 20 g/l, and according to yet another embodiment, the concentration of phenolic compounds is between 20 and 50 g/l.

Fermentation Broth and Use Thereof

A second aspect of the present invention relates to a fermentation broth comprising a lignocellulosic hydrolysate, at least one microbial growth inhibitor and an oleaginous microbe, wherein said oleaginous microbe is tolerant to said microbial growth inhibitor(s).

Preferably said least one microbial growth inhibitor is present in the lignocellulosic hydrolysate as a compound generated by the fractionation pre-treatment of the lignocellulosic material to obtain the lignocellulosic hydrolysate.

The content of the microbial inhibitor in the lignocellulosic hydrolysate (hemicellulose and cellulose fractions) and/or in the fermentation broth may thus be adjusted to reach the desired level in the fermentation broth. Preferably the at least one microbial inhibitor is the phenolic compounds of the lignocellulosic hydrolysate and the oleaginous microbe is an oleaginous microbe tolerant to the phenolic compounds present in the lignocellulosic hydrolysate.

Another aspect relates to the use of the fermentation broth of the present invention in a method for producing a microbial lipid.

Yet another aspect relates to the use of a composition comprising at least one microbial growth inhibitor in a method for producing a lipid, wherein the lipid is produced and accumulates in an oleaginous microbe and wherein said oleaginous microbe is tolerant to said at least one microbial growth inhibitor. In preferred embodiment the composition lignocellulosic hydrolysate and the at least one microbial inhibitor is the phenolic compounds present in the lignocellulosic hydrolysate to which said oleaginous microbe is tolerant.

In one preferred embodiment of the invention, the cultivation for microbial oil production on lignocellulosic hydrolysates is performed in non-sterile conditions. According, to another preferred embodiment of the invention the cultivation broth (also referred to as fermentation broth) containing lignocellulosic hydrolysate is heat treated, but not sterilized, such as pasteurized and used in single cell oil production process. According to another preferred embodiment of the invention, the heat treatment of broth containing lignocellulosic hydrolysate is an evaporation step used to concentrate sugars in lignocellulosic hydrolysates. The heat treatment combined (e.g. pasteurization and/or evaporation) together with inhibitory compounds derived from lignocellulose allow non-aceptic cultivation in single cell oil production.

When describing the embodiments of the present invention, the combinations and permutations of all possible embodiments have not been explicitly described. Nevertheless, the mere fact that certain measures are recited in mutually different dependent claims or described in different embodiments does not indicate that a combination of these measures cannot be used to advantage. The present invention envisages all possible combinations and permutations of the described embodiments.

The term "comprising", "comprise" and "comprises" herein are intended by the applicant to be optionally substituted with the terms "consisting of", "consist of" or "consists of", respectively, in every instance.

Items

In the following the invention is described by way of non-limiting items.

Item 1. A method for producing lipids, comprising the following steps
  (i) providing a cultivation medium comprising a lignocellulosic hydrolysate,
  (ii) providing a fermentation broth by inoculating the cultivation medium of (i) with a first microbe, where said first microbe is an oleaginous microbe,
  (iii) incubating said medium inoculated with said first microbe allowing lipids to accumulate, wherein said fermentation broth comprises at least one microbial growth inhibitor, and wherein said first microbe is tolerant to said microbial growth inhibitor(s), wherein said incubation is conducted under aerobic conditions.

Item 2. The method of item 1 further comprising a step of recovering the accumulated lipid from said first microbe.

Item 3. The method of item 1 or 2, wherein said fermentation broth further comprises a second microbe, which is intolerant to said at least one microbial growth inhibitor.

Item 4. The method according to item 3, wherein said second microbe is present in the cultivation medium provided in step (i) or contaminated the fermentation broth at step (ii) or (iii).

Item 5. The method according to any of the preceding items, wherein said second microbe is a non-oleaginous microbe.

Item 6. The method according to any of the preceding items, wherein said at least one microbial growth inhibitor is present in the cultivation medium provided in step (i).

Item 7. The method according to any of the preceding items, wherein said at least one microbial growth inhibitor is present in said fermentation broth at a concentration within the range of tolerance of said first microbe and outside the range of tolerance of said second microbe.

Item 8. The method according to any of the preceding items, further comprising a step of adding said at least one microbial growth inhibitor or adjusting the concentration of said at least one microbial growth inhibitor in the fermentation broth.

Item 9. The method according to any of the preceding items, wherein at least one microbial growth inhibitor is the group of phenolic compounds (measured as concentration of total phenols per volume of fermentation broth).

Item 10. The method according to item 9, wherein the level of said phenolic compounds in said fermentation broth is at least 1 g/l.

Item 11. The method according to item 9 or 10, wherein the level of said phenolic compounds in said fermentation broth is in the range of 1 g/l to 7 g/l or above (growth medium).

Item 12. The method according to any of item 9 to 11, wherein the level of said phenolic compounds in said fermentation broth is within the range of 1 g/l to 5 g/l, preferably within the range of 1 g/l to 3 g/l.

Item 13. The method according to any of the preceding items, wherein said first microbe is selected from the list consisting of filamentous fungi, yeast, bacteria and algae.

Item 14. The method according to any of the preceding items, wherein said first microbe is selected from the group consisting of *Mortierella, Aspergillus, Lipomyces, Rhodosporidium* and *Cryptococcus*.

Item 15. The method according to any of the preceding items, wherein said second microbe is non-oleaginous selected from the list consisting of bacteria yeast, filamentous fungi or microalgae.

Item 16. The method according to any of the preceding items, wherein said second microbe is a bacterium selected from the group consisting of *Bacillus* spp., *Pseudomonas* spp.

Item 16. The method according to any of the preceding items, wherein the cultivation medium comprising lignocellulosic hydrolysate provided in step (i) has not been sterilized.

Item 17. The method according to any of the preceding items, wherein the cultivation medium comprising a lignocellulosic hydrolysate provided in step (i) has not been subjected to a process of detoxification to remove said at least one growth inhibitor.

Item 18. The method of according to any of the preceding items, wherein the method is not performed under aseptic conditions.

Item 19. The method according to any of the preceding items, wherein said first microbe is capable of producing and accumulating more than fifteen percent of its weight as lipid (per cell dry weight).

Item 20. A fermentation broth comprising a lignocellulosic hydrolysate, at least one microbial growth inhibitor and an oleaginous microbe, wherein said oleaginous microbe is tolerant to said microbial growth inhibitor(s).

Item 21. Use of the fermentation broth of item 20 in a method for producing a lipid.

Item 22. Use of a composition comprising at least one microbial growth inhibitor in a method for producing a lipid, wherein the lipid is produced and accumulates in an oleaginous microbe and wherein said oleaginous microbe is tolerant to said at least one microbial growth inhibitor.

EXAMPLES

Preparation of Lignocellulosic Hydrolysates for Cultivations

Autohydrolysis Liquid A

Autohydrolysis liquid A was prepared by subjecting wheat straw to autohydrolysis treatment at 195° C. followed by steam explosion to ambient temperature and pressure. After the autohydrolysis, material was suspended in tap water to separate dissolving hemicellulosic sugars. Solid liquid separation was performed by pressure filtration to the suspension forming liquid phase containing hemicellulose and, a solid phase containing cellulose and lignin. The liquid phase (containing hemicellulosic sugars partly in oligomeric form) was concentrated to obtain autohydrolysis liquid A used in cultivation. Autohydrolysis liquid A contained 112 g/L sugars based on analysis by high-performance liquid chromatography (HPLC) and 13 g/L of phenolic compounds based on analysis with Folin-Ciocalteu method (Waterhouse, 2002).

In the cultivation experiment, the hydrolysate was diluted with water to obtain desired concentration of in the cultivation broth.

Autohydrolysis Liquid B

Autohydrolysis liquid B was prepared by from wheat straw with a treatment consisting of washing the straw followed by autohydrolysis. First wheat straw (38.1 kg DM) was washed in a 500 dm3 stirred-tank reactor with 80° C. water. The first solid fraction was separated from the first liquid fraction in a Seitz filter. The first solid fraction (34.7 kg DM) was manually loaded into a 500 dm3 reactor and mixed with water to give suspension at 8.6% consistency. The suspension was heated up to 175° C. (9.8 bar), and the pressure was released by opening the valve connected to the reactor. The second liquid fraction was separated from the second solid fraction in a decanter centrifuge. The second solid fraction was suspension-washed once with water and the third liquid fraction was separated from the washed solid fraction (128 kg having 16.9% dry matter content) was obtained. The second and third liquid fractions were combined, passed through bag filter, and the obtained filtrate (514 kg) was treated with activated carbon (4.1 kg) at room temperature. The liquid treated with activated carbon was clarified and concentrated in a falling film evaporator to give 23.8 kg of concentrated autohydrolysis liquid having 16.3% dry matter content and 18° Bx refractometric dry substance. The concentrated autohydrolysis liquid was again concentrated by evaporation to give autohydrolysis liquid B having pH 4.8 and 44.6% dry matter content of which the total carbohydrate content comprised 78.1% (w/w). The carbohydrate content was determined by high-performance liquid chromatography (HPLC) after dilute acid hydrolysis (4% w/w sulfuric acid, 121° C., 1 h) of the sample. The concentration of phenolic compounds was 31 g/L based on based on analysis with Folin-Ciocalteu method (Waterhouse, 2002).

After this the autohydrolysis liquid (containing hemicellulosic sugars partly in oligomeric form) was used in cultivation experiments as such.

Autohydrolysis Liquid C

The autohydrolysis reaction for wheat straw and subsequent isolation of hemicellulose oligosaccharides was carried out to produce liquid fraction for fermentation, and solid fraction susceptible for enzymatic hydrolysis. To achieve this, 35.7 kg wheat straw (89.8% dry matter content) was mixed with 240 kg of water giving suspension at 11.6% consistency in a 500 dm3 stirred tank reactor. The suspension was heated up to 180° C. followed by cooling to below 100° C. The hydrothermally treated suspension was discharged from the reactor and the first liquid fraction separated from the solid fraction using a decanter centrifuge. The solid fraction was suspension-washed in acidic water adjusted to pH 4 with phosphoric acid. The solid fraction was separated from the second liquid fraction in the decanter centrifuge. The first and second liquid fractions were combined and concentrated in a falling film evaporator to give 18.3 kg of concentrated autohydrolysis liquid forming autohydrolysis liquid C containing hemicellulose sugars partly in oligomeric from and having 42% dry matter content and 38° Bx refractometric dry substance. The washed solid fraction (96.7 kg having 23.0% dry matter content) was used as feed material for enzymatic hydrolysis to produce cellulose hydrolysate for cultivation.

Part of the phenolic compounds the autohydrolysis liquid concentrate contained were removed by treating the liquid by adding 40 g/l activated carbon, mixing gently for 20 hours in 4 C and finally filtering the carbon away using 400 um filtration cloth. This liquid was used in example 3 (purified autohydrolysis liquid C). In example 4, the hydrolyzate was used as such, with no purification.

Enzymatic hydrolysate from cellulose fraction of wheat straw was prepared from the solid fraction containing cellulose (after washing) from autohydrolysis experiment where autohydrolysis liquid C was prepared. The washed solid fraction from autohydrolysis treatment forming autohydrolysis liquid C (17.3 kg having 23.1% dry matter content) was weighed into a 40 dm3 stirred-tank reactor and mixed with 14.7 kg water and 10 mL 50% NaOH (w/w) to give suspension at 12.5% consistency and at pH 5. The reactor was heated up and maintained at 50° C. and 216 ml of enzyme mixture comprising 82% cellulose (Econase CE, Roal Oy), 10% cellobiase (Novozyme 188, Sigma/Novozymes) and 7% xylanase (GC140, Genencor). During the enzymatic treatment the suspension was stirred periodically three times per hour for 5 min. After 48 h residence time the suspension was supplemented with fresh enzyme mixture amounting 10% of the initial enzyme dosage and having similar proportions of individual enzymes. After 72 h residence time at 50° C. the liquid fraction was separated from the solid fraction by filtration using a hydropress. The solid fraction was washed once with water and the liquid fraction again separated from the solid fraction. The liquid fractions were combined and concentrated by evaporation under reduced pressure. The cellulosic hydrolysate concentrate (1.57 kg) contained 220 g/l total sugar.

The cellulose hydrosate containing monomeric sugars was used as such in cultivation.

Autohydrolysis Liquid D

A suspension was prepared by mixing 10.5 kg of milled wheat straw (92.7% dry matter content) and 54.1 kg of tap water in a 100 dm3 container. After storing at room temperature for 18 h, 64.2 kg of the suspension was weighed into a horizontal cylindrical 250 dm3 stirred autoclave reactor. The reactor was closed and heated within 75 min to 140° C., maintained at 140° C. for 5 h and cooled to room temperature within 30 min. The hydrothermally treated suspension was manually discharged from the reactor, and the first liquid fraction was separated from the first solid by filtration. The first solid fraction was washed twice with tap water and pressed using a hydro-press giving washed solid fraction. The washed solid fraction (20.9 kg) had 42.7% dry matter content. The first liquid fraction was combined with the wash-waters and concentrated in a falling film evaporator to 11.5% (w/w) dry matter content. The concentrated liquid, autohydrolysis liquid D, contained 49.3% total sugar from the total dry matter of the concentrated liquid as determined after dilute acid hydrolysis (4% w/w sulfuric acid, 121° C., 1 h) by high-performance liquid chromatography (HPLC). The relative proportions of anhydrous xylose, anhydrous arabinose, anhydrous glucose, and anhydrous galactose of the total sugar content were 57%, 19%, 13%, and 11%, respectively.

After this the autohydrolysis liquid D containing hemicellulosic sugars partly in oligomeric form was used in cultivation experiments as such.

Example 1—The Effect of Acetic Acid and Formic Acid on Fungal Growth

The experiments were done using a lipid producing fungal strain *Aspergillus. oryzae*. From the sporulating fungus grown on PDA-plates a spore suspension was made by adding 12 ml of sterile water and the spores were scraped off with inoculation loop to the liquid. The spore suspension was used for media inoculation.

The medium base components are presented in the table 1. All of them contained these basic nutrients, and small amount of fine cellulose to prevent the fungus from clumping.

TABLE 1

| Basic medium composition | |
| --- | --- |
| | g/l |
| Cellulose | 2 |
| malt extract | 30 |
| Peptone | 3 |

The medium was made using tap water.

The organic acids were added in so the concentration of the formic and acetic acid alone was 0, 1, 3, 5 and 7 g/l, and for the two acids together 0, 1, 3, 5, 7 and 9 g/l. After this the pH of the media was adjusted to 5.5-6.0 using 3 M NaOH. The medium was distributed to 50 ml batches into 250 ml erlenmayer flasks. The media was sterilized in autoclave 121 C 15 min. After cooling down, each flask was inoculated using 0.5 ml spore suspension mentioned earlier. For each concentration, parallel cultivations were made. The cultivations were incubated in 160 rpm shaking at 28 C 5 days. The growth was observed daily with a microscope, and in the end of the cultivation the biomass and lipid contents were determined.

The biomass content was determined by vacuum filtering the whole content of the flask and washing the biomass with 50 ml of distilled water. After this the biomass cakes were frozen and dried overnight in freeze dryer. From the dries biomass the lipid content was analyzed according to Suutari et al. (1990). The lipids in the samples were first hydrolysed into free fatty acids, which were saponified into sodium salts thereof and thereafter methylated into methyl esters. The fatty methyl esters were analysed gas chromatographically.

Results: In all flasks regardless of acid concentration the growth began almost at the same time. The biomass and lipid concentrations were also very similar. Based on these results it could be stated that the acids tested, separate or together, had no effect on fungal growth or lipid production. The biomass and lipid concentrations are presented in table 2.

TABLE 2

Biomass concentrations and lipid contents in different acid concentrations.

| | Biomass concentration g/l | Lipid content (% from cell dry weight) |
| --- | --- | --- |
| Acetic acid concentration g/l | | |
| 0 | 12.4 | 20.1 |
| 1 | 12.4 | 19.8 |
| 3 | 11.4 | 20.7 |
| 5 | 11.1 | 21.2 |
| 7 | 11.5 | 24.3 |
| Formic acid concentration (g/l) | | |
| 0 | 12.9 | 18.9 |
| 1 | 12.5 | 19.5 |
| 3 | 12.0 | 19.5 |
| 5 | 11.2 | 15.9 |
| 7 | 10.9 | 19.8 |
| Concentration of both acetic and formic acid (g/l) | | |
| 0 | 12.9 | 18.9 |
| 1 | 12.4 | 20.3 |
| 3 | 11.6 | 18.1 |
| 5 | 11.0 | 22.0 |
| 7 | 10.4 | 17.4 |
| 9 | 9.5 | 15.9 |

Example 2—The Inhibiting Effect of Phenolic Compounds

The experiments were done using producing fungal and yeast strains *Aspergillusoryzae, Mortierella. isabellina* and *Lipomyces starkeyi*. Two different lignocellulosic hydrolysates from autohydrosis treatment of lignocellulose containing hemicellulosic sugars and notable amounts of phenolics were tested, autohydrolysis liquid e A and autohydrolysis liquid B. The phenolic compounds were determined according to the Folin-Ciocalteu method with gallic acid as standard (Waterhouse, 2002).

From the sporulating fungus grown on PDA-plates a spore suspension was made by adding 12 ml of sterile water and the spores were scraped off with inoculation loop to the liquid. The spore suspension was used for media inoculation.

The medium base components are presented in the table 3. All of them contained these basic nutrients, and small amount of fine cellulose to prevent the fungus from clumping.

TABLE 3

Composition of growth medium

|  | g/l |
|---|---|
| glucose | 20 |
| malt extract | 30 |
| peptone | 3 |

The medium was made using tap water.

The autohydrolysis liquid A or B was added in so that the concentration of phenolics was 0, 1, 2, 3, 4, 5, 6 and 7 g/l. After this the pH of the media was adjusted to 6.5 using 3 M NaOH. The medium was distributed to 50 ml batches into 250 ml erlenmayer flasks. The media was sterilized in autoclave 121 C 15 min. After cooling down, each flask was inoculated using 0.5 ml spore suspension mentioned earlier in the case of fungi, and with the yeast pre-cultured yeast suspension was used. For each concentration, parallel cultivations were made. The fungal cultivations were incubated in 160 rpm shaking, and the yeasts in 160 rpm, all at 28 C for 5 days. The growth was observed twice daily with a microscope, and in the end of the cultivation the biomass contents were determined.

The fungal biomass content was determined by vacuum filtering the whole content of the flask and washing the biomass with 50 ml of distilled water. After this the biomass cakes were frozen and dried overnight in freeze dryer and the biomass content was determined.

The yeast biomass content was determined by measuring to pre-weighted tubes 7 ml of test growth suspension, parallel samples from each flask. The samples were centrifuged 6000 rpm for 10 min, after which the supernatant was removed, 7 ml of distilled water was added, the tube content was well mixed and the centrifugation repeated. The washing water was then removed, and both the biomass pellets and the supernatants were frozen. Later on, the biomass samples were freeze dried and the biomass content was determined.

Results:

By microscopic observations it could be seen that when the phenolic concentration rose, the time needed for the growth to begin grew a little longer with some microbes. The cultivations were monitored twice in a day, so determining the exact moment when the growth began is not possible, but rough estimations can be made. With the yeast *L. starkeyi* and the fungus *A. oryzae* there was no notable lag in any of the tested phenolic concentrations, and all were growing after one day of incubation. The fungus *M. isabellina* on the other hand the growth began more slowly when the phenolic concentration rose above 4 g/l.

*A. oryzae* could grow even in the highest phenolic concentration tested: 7 g/l, but the biomass content was decreasing when the phenolic concentration grew higher. *L. starkeyi* and *M. isabellina* could grow up to 6 g/l concentration, in 7 g/l no growth was detected. Similar to *A. oryzae*, the biomass content was decreasing when the phenolic concentration grew higher. No differences between different hydrolysates from autohydrolysis inhibition were detected. In the following table, the biomass content for the microbes tested in various phenolic concentrations are given.

TABLE 4

Biomass content for the microbes tested in different phenolic concentrations.

| Microbe | Autohydrolysis liquid | Phenolics concentration (g/l) | Biomass concentration (g/l) |
|---|---|---|---|
| Mortierella isabellina | A | 0 | 12.4 |
| Mortierella isabellina | A | 1 | 10.7 |
| Mortierella isabellina | A | 2 | 10.4 |
| Mortierella isabellina | A | 3 | 7.4 |
| Mortierella isabellina | A | 4 | 5.1 |
| Mortierella isabellina | A | 5 | 1.5 |
| Mortierella isabellina | A | 6 | 0 |
| Mortierella isabellina | A | 7 | — |
| Aspergillus oryzae | A | 0 | 15.0 |
| Aspergillus oryzae | A | 1 | 15.4 |
| Aspergillus oryzae | A | 2 | 13.2 |
| Aspergillus oryzae | A | 3 | 11.4 |
| Aspergillus oryzae | A | 4 | 11.8 |
| Aspergillus oryzae | A | 5 | 11.2 |
| Aspergillus oryzae | A | 6 | 11.1 |
| Aspergillus oryzae | A | 7 | 7.6 |
| Lipomyces starkeyi | A | 0 | 14.7 |
| Lipomyces starkeyi | A | 2 | 13.8 |
| Lipomyces starkeyi | A | 3 | 10.1 |
| Lipomyces starkeyi | A | 4 | 8.5 |
| Lipomyces starkeyi | A | 5 | 3.7 |
| Lipomyces starkeyi | A | 6 | 0.6 |
| Mortierella isabellina | B | 0 | 12.54 |
| Mortierella isabellina | B | 2 | 7.7709 |
| Mortierella isabellina | B | 3 | 6.4339 |
| Mortierella isabellina | B | 4 | 4.9039 |
| Mortierella isabellina | B | 5 | 3.8129 |
| Mortierella isabellina | B | 6 | 0.6259 |
| Mortierella isabellina | B | 7 | — |
| Aspergillus oryzae | B | 0 | 14.9 |
| Aspergillus oryzae | B | 3 | 9.5 |
| Aspergillus oryzae | B | 4 | 8.0 |
| Aspergillus oryzae | B | 5 | 6.8 |
| Aspergillus oryzae | B | 6 | 6.8 |
| Aspergillus oryzae | B | 7 | 5.3 |
| Lipomyces starkeyi | B | 0 | 14.7 |
| Lipomyces starkeyi | B | 2 | 10.4 |
| Lipomyces starkeyi | B | 4 | 6.5 |
| Lipomyces starkeyi | B | 5 | 5.6 |
| Lipomyces starkeyi | B | 6 | 3.3 |

Example 3—Fungal Growth and Lipid Production on Wheat Straw Hemicelluse and Cellulose Hydrolysate Sugars The experiments were done using a lipid producing fungal strain *A. oryzae*. From the sporulating fungus grown on PDA-plates a spore suspension was made by adding 12 ml of sterile water and the spores were scraped off with inoculation loop to the liquid. 24 ml of the spore suspension was directly used for fermentor inoculation. The medium composition is presented in table 5. Purified autohydrolysis liquid C (hemicellulose solution) and the cellulose hydrolysate from the same experiment was used in the cultivation. The cultivation was done in Biostat B plus 5 l fermentor in 3 l volume, and during it the stirring was set to 500 rpm, pH was kept in 5.5 with 3 M NaOH, the aeration was 1 vvm and the temperature 35 C during growth, in lipid production it was lowered to 28 C.

TABLE 5

Composition of growth medium

| Medium components | Concentration (g/l) |
|---|---|
| Hemicellulosic sugars | 20 |
| Yeast extract | 2 |
| (NH4)2SO4 | 1.5 |
| MgCl * 6 H2O | 1.5 |
| K2HPO4 | 0.8 |
| KH2PO4 | 1.5 |
| CaCl2* 2H2O | 0.3 |

After inoculation it took about 30 h before the fungus started growing actively. During cultivation, the hemicellulose solution was added in small batches, and after 95 h of cultivation the feeds were changed to cellulosic hydrolyzate. During the cultivation, in total 236 g of hemicellulose and 484 g cellulose hydrolyzate was added. Part of the sugars added was left unutilized at the end of the fermentation. At 167 h, when the cultivation ended, there was 16 g/l of biomass, of which 43% lipids (FIG. 1). It could be concluded that producing microbial oil from wheat straw hemicellulose and cellulose sugars was successful. In the beginning of the fermentation the phenolic concentration was 4 g/l, and in the end 6 g/l (a calculation based on original amount of hemicellulose). Therefore, it could also be stated that fungal growth and efficient lipid production was achieved in spite of high inhibitor concentrations.

Example 4—The Growth of Contaminating Bacteria on Phenolic Containing Hemicellulosic Solution The experiments were done with the bacteria *Bacillus subtilis* and *Pseudomonas fluorescens*. The medium base components are presented in the table 6. All of them contained these basic nutrients, and phenolic compounds containing hemicellulose solution so that the final concentration of phenolics was 0, 1, 2 and 3 g/l. Autohydrolysis liquid C (hemicellulose solution) was used in the cultivation and it contained 160 g/l sugars based on HPLC analysis, DW 460 g/l and 33 g/l phenolics based on analysis with Folin-Ciocalteu method (Waterhouse, 2002).

TABLE 6

Composition of growth medium

| | g/l |
|---|---|
| glucose | 20 |
| malt extract | 30 |
| peptone | 3 |

The medium was made using tap water.

The autohydrolysis liquid C (hemicellulose solution) was added in so that the concentration of phenolics was 0, 1, 2 and 3 g/l. After this the pH of the media was adjusted to 6.5 using 3 M NaOH. The medium was distributed to 50 ml batches into 250 ml erlenmayer flasks. The media was sterilized in autoclave 121 C 15 min. After cooling down, each flask was inoculated using 0.5 ml of pre-cultured bacteria suspension. For each concentration, parallel cultivations were made. The cultivations were incubated in 250 rpm shaking, at 28 C for 5 days. The growth was observed daily with a microscope, and in the end of the cultivation the glucose contents were determined. The sugar concentration samples were made by centrifuging the biomass down, diluting the supernatant by 10 with distilled water and HPLC analysis was made.

Results:

Based on microscope observations it could be seen that both bacteria grew only in those flasks which contained no phenolics. At the end of the cultivation only in the flasks that contained no phenolics all sugars were consumed. In flasks that contained phenolics, the same amount of sugars as in the beginning was present. It could be concluded that even in small concentrations the phenolic compounds inhibit efficiently the growth of many contaminating bacteria. It can be concluded that growth of contaminating bacteria can be inhibited or prevented by using lignocellulosic hydrolysates containing inhibitory compounds, such as phenolic, compounds in concentrations which do not significantly inhibit growth of oleaginous yeast and filamentous fungi (examples 2, 3 and 6).

Example 5—Controlling the Contaminations with the Help of Phenolic Compounds and Quick Heat Treatment The experiments were done using a lipid producing fungal strain *A. oryzae*. From the sporulating fungus grown on PDA-plates a spore suspension was made by adding 12 ml of sterile water and the spores were scraped off with inoculation loop to the liquid. 0.5 ml of the spore suspension was used for each flask inoculation. The medium composition is presented in table 9.

The phenolics containing liquid from autohydrolysis, autohydrolysis liquid A (hemicellulose solution), was added so that the final concentration in the media was 3.5 g/l. After this the pH of the media was adjusted to 6.5 using 3 M NaOH. The medium was distributed to 50 ml batches into 250 ml erlenmayer flasks. The yeast extract here was used as a source for usual contaminating microbes.

TABLE 9

Growth medium composition

| | g/l |
|---|---|
| Glucose | 40 |
| Phenolics | 3.5 |
| Yeast extract | 5 |
| (NH4)2SO4 | 2 |
| MgSO4 * 7 H2O | 1.0 |
| K2HPO4 | 0.5 |
| KH2PO4 | 1.0 |
| CaCl2* 2H2O | 0.2 |

Half of the media prepared this way was quickly heated to 80 C, and then cooled down. For the rest of the media, no heat treatment was made. Half of the each differently treated flasks were inoculated with 0.5 ml of *A. oryzae* spore suspension. The other half of the flasks were left uninoculated. Also, two flasks of above described medium without phenolics addition was made. This was heat treated in 80 C and inoculated as other cultivations. All the cultivations were incubated in 28 C and 160 rpm shaking for 7 days. Microbial growth was checked daily with microscope.

Results:

After 1 day of incubation it was observed that the fungus grew in all the media that was inoculated with the spore suspension. In the flasks which were not heat treated with spores and contained no phenolics there was notable amount of different contaminating bacteria and yeasts. None of the phenolics containing media were contaminated. After 2 days of incubation in the flasks which were nor inoculated or heat treated, contaminating yeast had started to grow. At the end of the cultivations the fungus had grown well in all the flasks that were inoculated with spores. No contaminating microbes were detected amongst them. In the uninoculated and flasks which were not heat treated, was detected also a bacterial contamination besides yeasts mentioned earlier. Contrary to this, the flasks which contained no inocula but were heat treated remained growth free until end of the experiments.

Based on these results, 80° C. heat treatment together with the addition of phenolic compounds would seem to be able to keep hemicellulose based cultivations free of most common contaminating microbes. On the other hand, it must be noted that without phenolics the growth medium without heat treatment is easily contaminated, so from hygiene point of view both operations, the addition of phenolic compounds and light heat treatment are needed.

Example 6—Producing Microbial Oil on Hemicellulosic Sugars

The experiments were done using a lipid producing fungal strain *A. oryzae*. From the sporulating fungus grown on PDA-plates a spore suspension was made by adding 12 ml of sterile water and the spores were scraped off with inoculation loop to the liquid. 24 ml of the spore suspension was used for inoculation of 6 flasks. The medium composition is presented in table 10. The inoculated flasks were incubated at 30 C 160 rpm shaking for 1 day, and then used for fermentor inoculation.

TABLE 10

Composition of inoculation medium, pH set to 5.5.

| | g/l |
|---|---|
| Hemicellulosic sugars | 40 |
| Yeast extract | 1 |
| (NH4)2SO4 | 1 |
| MgSO4 * 7 H2O | 1 |
| K2HPO4 | 0.5 |
| KH2PO4 | 1 |
| CaCl2* 2H2O | 0.2 |

Autohydrolysis liquid D (containing hemicellulosic sugars partly in oligomeric form) was used and it contained 4.2 g/l phenolic compounds based on analysis with Folin-Ciocalteu method (Waterhouse, 2002). The cultivation was done in Biostat B plus 5 l fermentor in 3 l volume, and during it the stirring was set to 400 rpm, pH was kept in 5.5 with 3 M NaOH, the aeration was 1 vvm and the temperature 30 C. The medium composition is presented in table 11.

TABLE 11

The composition of fermentation medium

| Medium components | Concentration (g/l) |
|---|---|
| Hemicellulosic sugars | 60 |
| Yeast extract | 1 |
| (NH4)2SO4 | 1 |
| MgCl * 6 H2O | 1.0 |
| K2HPO4 | 0.5 |
| KH2PO4 | 1.0 |
| CaCl2* 2H2O | 0.2 |

Results:

During cultivation, the hemicellulosic solution was added in small batches. In total 150 g of hemicellulose was added. Part of the sugars added was left unutilized at the end of the fermentation. At 142 h, when the cultivation ended, there was 14 g/l of biomass, of which 21% lipids. It could be concluded that producing microbial oil from wheat hemicellulosic sugars (partly in oligomeric form) was successful. In the fermentation the concentration of phenolic compounds was 2.8 g/L. Therefore, it could also be stated that fungal growth and lipid production was possible in spite of high inhibitor concentrations.

Example 7—Effect of Furfural on Microbial Growth

Cultivation Conditions

Two fungal strains *Aspergillus oryzae* TKK-4 and *Mortierella isabellina* TKK-1 and one yeast strain *Lipomyces starkeyi* TKK-1 were cultivated in flasks in a standard medium (Table 12) with furfural addition. The microorganisms were grown for 6 days in 28° C. with 160 rpm (for fungi) and 250 rpm (for yeast). Cellulose was added to help the fungus grow with a better morphology. Furfural was added in different amounts into the medium (0-4 g/l) and the growth of the microorganisms was observed.

TABLE 12

Medium components.

| Medium component | g/l |
|---|---|
| Malt extract | 30 |
| Peptone | 3 |
| Dextrose monohydrate | 20 |
| Cellulose | 2 |

Results

After one week *A. oryzae* TKK-4 grew in 0.5 g/l furfural, but higher concentrations (≥0.75 g/l) inhibited the growth completely. *M. isabellina* TKK-1 did not grow in ≥1 g/l furfural, but after 4-6 days some growth was observed in 0.8 g/l. *L. starkeyi* TKK-1 was most tolerant towards furfural. It grew in 1.2 g/l furfural after a few days. The inhibiting concentration was ≥1.8 g/l. Table 13 shows the dry weight concentrations for the flask cultivations with the furfural concentration of 0-1.2 g/l.

TABLE 13

The dry weight concentration measured after 6 days of cultivation in fungi *A. oryzae* TKK-4 and *M. isabellina* TKK-1 and yeast *L. starkeyi* TKK-1, when the furfural concentration was 0-1.2 g/l.

| Furfural (g/l) | *A. oryzae* TKK-4 | *M. isabellina* TKK-1 DW (g/l) | *L. starkeyi* TKK-1 |
|---|---|---|---|
| 0 | 18.02 | 16.17 | 14.46 |
| 0.1 | 18.18 | | |
| 0.2 | 16.54 | 7.02 | |
| 0.3 | 13.53 | | |
| 0.4 | 11.58 | 13.80 | |
| 0.6 | | 14.96 | 14.79 |
| 0.8 | | 9.28 | |
| 1.2 | | | 14.39 |

Example 8—Autohydrolysis (with Pre-Adjusted pH) of Wheat Straw

A suspension was prepared by mixing 20 g wheat straw previously milled to pass a 1 mm screen and 180 g water.

The suspension was adjusted with acetic acid to pH 4.5. The suspension was transferred into an autoclave reactor that was then non-isothermally heated up with a heating jacket to temperature between 170° C. and 200° C. with continuous stirring. The temperature data during the heating was recorded and used to calculate autohydrolysis severity (Eq. 1). The reactor was cooled to approximately 50 C, and the suspension was manually recovered for filtration. The liquid fraction was separated from the solid fraction and furfural and hydroxymethyl furfural (HMF) in the liquid fraction were measured using HPLC. Total concentration of sugar (g/l) in the liquid fraction was determined after dilute acid hydrolysis that converts oligomeric and polymeric sugars into monosaccharides. The solid fraction was washed with water (0.5 dm3) and pressed. The obtained solid residue was weighed, sampled for dry matter determination, and the yield of solid residue (%) was calculated as the weight ratio of solid residue to the wheat straw weighed to the autohydrolysis treatment (100%*g dry wheat straw/g dry solid residue). Soluble phenolic substances in the liquid were determined using the Folin-ciocalteu method with guiaiacol as standard.

Figure 2:
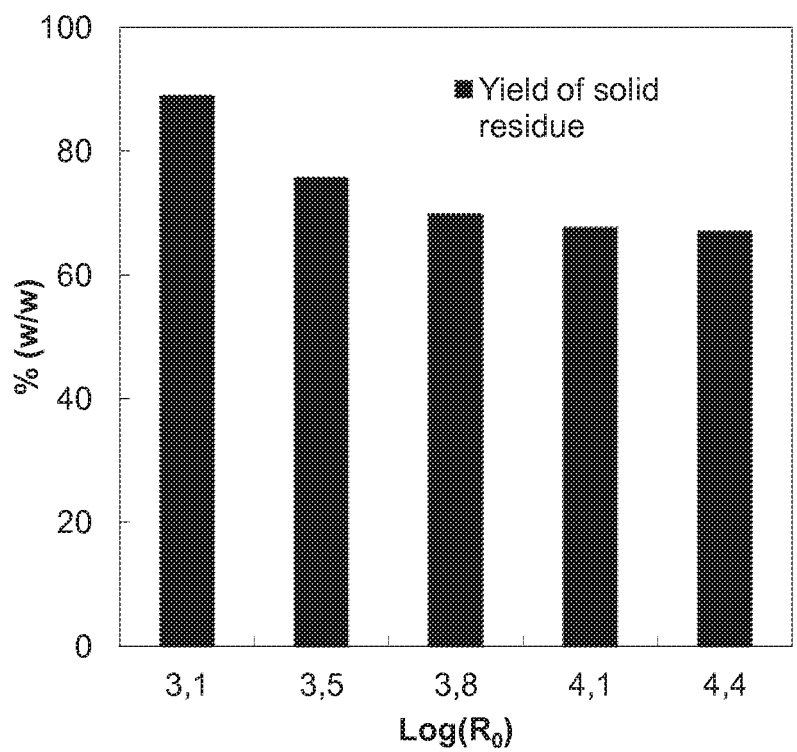
FIG. 2 presents the yield of solid residue from autohydrolysis of wheat straw.
Figure 3:
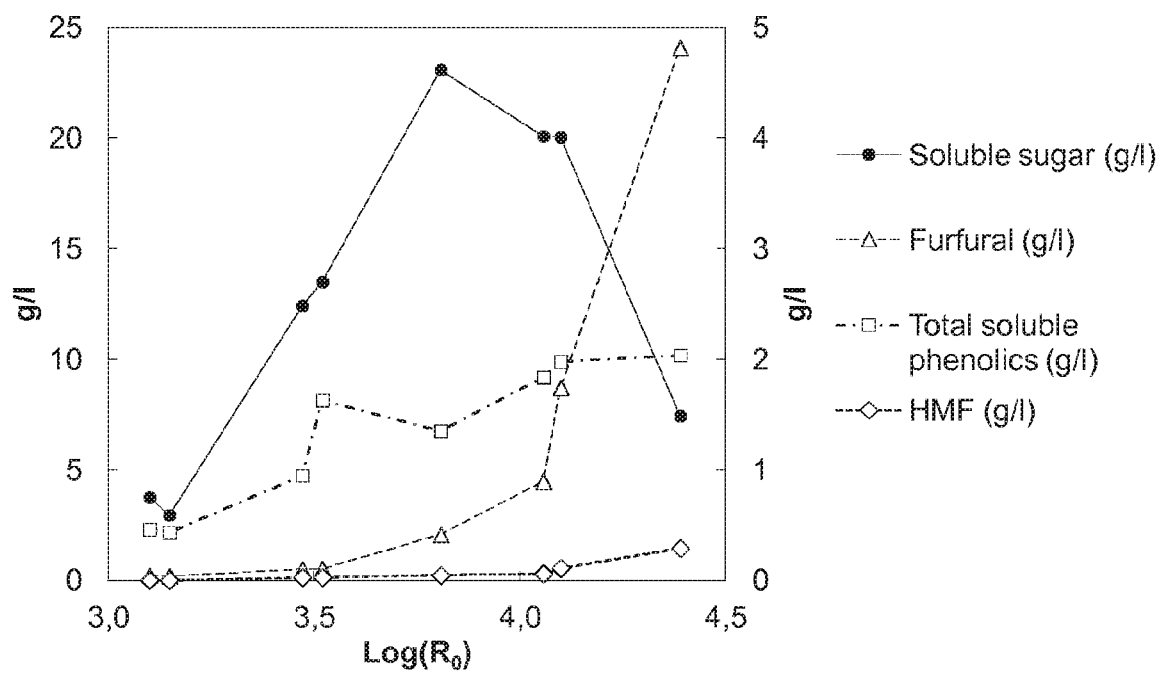
FIG. 3 presents the concentration of total soluble sugar (g/l, left y-axis) and potential microbial inhibitor substances; furfural, hydroxymethyl furfural (HMF) and soluble phenolics (g/l, right y-axis) in the liquid fraction obtained from autohydrolysis of what straw at 10% consistency (g straw solids dry matter/g total).

The results shown in FIG. 2 and FIG. 3 summarize the results. The yield of solid residue decreased with autohydrolysis severity with 67% yield at the highest severity (Log(R0)=4.4) (FIG. 2). The concentration of monosaccharide sugars in the liquid fraction first increased and then decreased with increasing autohydrolysis severity. The maximum concentration of sugar (23.1 g/l) was obtained when autohydrolysis severity was Log(R0)=3.8. Beyond this autohydrolysis severity the concentration of sugar in the liquid fraction drastically decreased and concentration of furfural and HMF suddenly increased reaching concentration of 4.8 g/l and 0.3 g/l, respectively. In contrast to the sudden generation of furfural and HMF, the concentration of soluble phenolics increased progressively from 0.5 g/l up to 2.0 g/l with increasing autohydrolysis severity.

This example shows that optimal autohydrolysis conditions in terms of autohydrolysis severity (Log(R0)) can be selected to avoid excess formation of furfural, HMF, and soluble phenolics while maximizing the concentration of monosaccharides in the liquid fraction.

REFERENCES

Suutari, M., Liukkonen, K. ja Laakso, S., Temperature adaptation in yeasts: the role of fatty acids, J. Gen. Microbiol. 136 (1990) 1496-1474.

Waterhouse A L. 2002. Determination of total phenolics. In: Wrolstad R E, Acree T E, An H, Decker E A, Penner M H, Reid D S, Schwartz S J, Shoemaker C F, Sporns P, editors. Current protocols in food analytical chemistry. 1st ed. New York: John Wiley & Sons, Inc. p 11.1.1-11.1.8.

The invention claimed is:

1. A method for producing lipids, comprising:
   (i) providing a cultivation medium having a lignocellulosic hydrolysate,
   (ii) providing a fermentation broth by inoculating the cultivation medium of (i) with a first microbe, where said first microbe is an oleaginous microbe,
   (iii) incubating said medium inoculated with said first microbe to allow lipids to accumulate, wherein said fermentation broth includes at least one microbial growth inhibitor, and wherein said first microbe is tolerant to said microbial growth inhibitor(s), wherein said incubation is conducted under aerobic conditions,
   (iv) adding said at least one microbial growth inhibitor or adjusting the concentration of said at least one microbial growth inhibitor in the fermentation broth, wherein said fermentation broth comprises a second non-oleaginous microbe which is intolerant to said at least one microbial growth inhibitor, whereas said microbial growth inhibitor is present in said fermentation broth at a concentration within a range of tolerance of said first microbe and outside a range of tolerance of said second microbe,
   (v) collecting accumulated lipids.

2. The method according to claim 1, wherein said second microbe is present in the cultivation medium provided in step (i) or contaminated the fermentation broth at step (ii) or (iii).

3. The method according to claim 1, wherein at least one microbial growth inhibitor is a phenolic compound measured as concentration of total phenols per volume of fermentation broth.

4. The method according to claim 3, wherein a level of said phenolic compound in said fermentation broth is at least 1 g/l.

5. The method according to claim 3, wherein a level of said phenolic compound in said fermentation broth is in a range of 1 g/l to 7 g/l or above.

6. The method according to claim 3, wherein a level of said phenolic compound in said fermentation broth is within a range of 1 g/l to 5 g/l.

7. The method according to claim 1, wherein said first microbe is selected from the group consisting of: filamentous fungi, yeast, bacteria and algae.

8. The method according to claim 1, wherein said first microbe is selected from the group consisting of: *Mortierella, Aspergillus, Lipomyces, Rhodosporidium* and *Cryptococcus*.

9. The method according to claim 1, wherein said second microbe is non-oleaginous selected from the group consisting of: bacteria, yeast, filamentous fungi or microalgae.

10. The method according to claim 1, wherein said second microbe is a bacterium selected from the group consisting of: *Bacillus* spp., *Pseudomonas* spp.

11. The method according to claim 1, wherein said first microbe is selected for producing and accumulating more than fifteen percent of its weight as lipid.

12. The method according to claim 3, wherein a level of said phenolic compound in said fermentation broth is within a range of 1 g/l to 3 g/l.

* * * * *